US008945828B2

(12) United States Patent
Kolvraa et al.

(10) Patent No.: US 8,945,828 B2
(45) Date of Patent: Feb. 3, 2015

(54) METHOD OF IDENTIFYING FETAL ANTIGENS OR CELL SURFACE MARKERS USING PHAGE DISPLAY TECHNOLOGY

(75) Inventors: Sten Kolvraa, Skoedstrup (DK); Britta Christensen, Birkeroed (DK); Palle Schelde, Hoejbjerg (DK); Morten Draeby Sorensen, Aahus N. (DK); Peter Kristensen, Tranbjerg (DK)

(73) Assignee: Aarhus Universitet, Århus C (DK)

( * ) Notice: Subject to any disclaimer, the term of this patent is extended or adjusted under 35 U.S.C. 154(b) by 16 days.

(21) Appl. No.: 13/169,922

(22) Filed: Jun. 27, 2011

(65) Prior Publication Data
US 2012/0070827 A1    Mar. 22, 2012

Related U.S. Application Data

(63) Continuation of application No. 12/096,594, filed as application No. PCT/DK2006/000693 on Dec. 7, 2006, now abandoned.

(30) Foreign Application Priority Data

Dec. 8, 2005   (DK) .................................. 2005 01745

(51) Int. Cl.
| | |
|---|---|
| C12Q 1/70 | (2006.01) |
| C12Q 1/68 | (2006.01) |
| G01N 33/53 | (2006.01) |
| G01N 33/566 | (2006.01) |
| C12N 5/00 | (2006.01) |
| C12N 15/10 | (2006.01) |

(52) U.S. Cl.
CPC ............ *C12Q 1/6879* (2013.01); *C12N 5/0081* (2013.01); *C12N 15/1037* (2013.01); *C12Q 1/6806* (2013.01); *C12Q 1/6841* (2013.01); *G01N 33/566* (2013.01)
USPC ................... 435/5; 435/4; 435/6.1; 435/6.13; 435/7.1

(58) Field of Classification Search
None
See application file for complete search history.

(56) References Cited

U.S. PATENT DOCUMENTS

| | | | |
|---|---|---|---|
| 5,648,222 A | 7/1997 | Tse et al. | |
| 6,773,903 B2 * | 8/2004 | Bova .......................... | 435/173.7 |
| 2003/0036100 A1 | 2/2003 | Fisk et al. | |
| 2005/0049793 A1 | 3/2005 | Paterlini-Brechot | |

FOREIGN PATENT DOCUMENTS

| | | |
|---|---|---|
| WO | WO-9503431 | 2/1995 |
| WO | WO-9730354 | 8/1997 |

OTHER PUBLICATIONS

Emmert-Buck et al., Science, 1996; 274: 998-1001.*
Tortura et al., "The Nature of Antigens", in Microbiology, An Introduction, Sixth Edition, Addison Wesley Longman, Inc. p. 463-464.*
Shibata et al., Amer J Path. 1992; 141: 539-543.*
P. 18 of Molecular Biology of the Cell, Alberts et al., 1994; Garland Publishing, Inc., 717 Fifth Avenue, New York, NY 10022.*
Sørensen et al., J. Cell. Mol. Med. 2010; 14: 1953-1961.*
Marasco and Sui, Nature Biotechnology, 2007; 25: 1421-1434.*
Ager et al., "Retroviral display of antibody fragments; interdomain spacing strongly influences vector infectivity", *Human Gene Therapy*, vol. 7 (Nov. 1996): 2157-2164.
Boder et al., "Yeast surface display for screening combinatorial polypeptide libraries", *Nature Biotechnology*, vol. 15 (Jun. 1997): 553-557.
Buchholz et al., "In vivo selection of protease cleavage sites from retrovirus display libraries", *Nature Biotechnology*, vol. 16 (Oct. 1998): 951-954.
Carter et al., "High level *Escherichia coli* expression and production of a bivalent humanized antibody fragment", Biotechnology, vol. 10: 163-167, Feb. 1992.
Cirigliano et al., "Rapid prenatal diagnosis of common chromosome aneuploidies by OF-PCR. Assessment on 18000 consecutive clinical samples", *Molecular Human Reproduction*, 10.11, Sep. 2004: 839-846.
Cumber et al., "Comparative Stabilites in Vitro and in Vivo of a Recombinant Mouse Antibody FvCys Fragment and a bisFvCys Conjugate", *The Journal of Immunology*, 149.1, (Jul. 1992): 120-126.
Francisco et al., "Production and flourescence-activated cell sorting of *Escherichia coli* expressing a functional antibody fragment on the external surface", *Biochemistry*, vol. 90 (Nov. 1993): 10444-10448.
Georgiou et al., "Display of heterologous proteins on the surface of microorganisms: From the screening of combinatorial libraries to live recombinant vaccines", *Nature Biotechnology*, vol. 15 (Jan. 1997): 29-34.
Gold, Larry, "mRNA display: Diversity matters during in vitro selection", PNAS, 98.9 (Apr. 2001): 4825-4826.
Christensen et al., Studies on the isolation and identification of fetal nucleated red blood cells in the circulation of pregnant women before and after chorion villus sampling, *Fetal Diag Ther*, 18: 378-384, 2002.
Voullaire et al., Fetal nucleated red blolod cells from CVS washings: an aid to development of first trimester non-invasive prenatal diagnosis, *Prenat Diag*, 21: 827-34, 2001.
Christensen et al., *Fetal Diagn Ther*, 18: 470-484, 2003.
Vallejo et al., *Anesthesiology Abstracts*, 103: A565, Oct. 24, 2005.
Archived chat from Purdue University dated Feb. 25, 1997; downloaded on Dec. 15 from purdue.edu/pipermail/cytometry/1997-February/006534.html; 1 page.

(Continued)

*Primary Examiner* — Christina Borgeest
(74) *Attorney, Agent, or Firm* — Gifford, Krass, Sprinkle, Anderson & Citkowski, P.C.

(57) ABSTRACT

The present application relates to methods for identification of foetal cells and generation and isolation of binding members recognizing foetal cells. The methods of the invention may further be used for other purposes relating to characterization of biological samples and biological antigens. The methods are characterized by the applicability in situations where the interesting objects are present in a limited amount, or where the interesting objects are intermixed with other material, thus the methods are suitable for use in situations where the ratio of the interesting material compared to other material is low.

19 Claims, 9 Drawing Sheets

(56) References Cited

OTHER PUBLICATIONS

Greenberg et al., A new antigen receptor gene family that undergoes rearrangement and extensive somatic diversification in sharks, *Letter to Nature*, vol. 374 (Mar. 1995): 168-173.

Griffiths et al., "Isolation of high affinity human antibodies directly from large synthetic repertoires", *The EMBO Journal*, 13.14 (1994): 3245-3260.

Hamers-Casterman et al., "Naturally occurring antibodies devoid of light chains", *Letters to Nature*, vol. 363 (Jun. 1993): 446-44B.

Hanes et al., "In vitro selection and evolution of functional proteins by using ribosome display", *Biochemistry*, vol. 94 (May 1997): 4937-4942.

Huie et al., "Antibodies to human fetal erythroid cells from a nonimmune phage antibody library", *PNAS*, 98.5 (Feb. 2001): 2682-2687.

Jensen et al, "Functional improvement of antibody fragments using a novel phage coat protein III fusion system," *Biochemical and Biophysical Research Communications*, vol. 298 (2002): 566-573.

Khosrotehrani et al.. "Multi-lineage potential of fetal cells in maternal tissue: a legacy in reverse", *Journal of Cell Science*, 118.8 (2005): 1559-1563.

Kristensen et al., "Proteolytic selection for protein folding using filamentous bacteriophages", *Folding and Design*, 3.5 (Jul. 1998): 321-328.

Llpovsek el al., "In-vitro protein evolution by ribosome display and mRNA display", *Journal of Immunological Methods*, vol. 290 (2004): 51-67.

Lu et al., "Oral and maxillofacial pathology: Application of laser capture microdissection to phage display peptide library screening", Oral Surgery, Oral Medicine, Oral Pathology, Oral Radiology, and Endodontology, 98.6 (Dec. 2004): 692-97.

McCfferty et al., "Phage antibodies: filamentous phage displaying antibody variable domains", *Letters to Nature*, vol. 348 (Dec. 1990): 552-554.

Odegrip et al., "CIS display: In vitro selection of peptides from libraries of protein—DNA complexes", PNAS, 101.9 (Mar. 2004): 2806-2810.

Pack et al., "Miniantibodies: Use ofamphipathic helices to produce functional, flexibly linked dimeric fragments with high avidity in *Escherichia coli*", *Biochemistry*, 31.6 (Feb. 1992): 1579-1584.

Parsons et al., "Directing phage selections toward specific epitopes", *Protein Engineering*, 9.11 (1996): 1043-49.

Smith, George P., "Filamentous fusion phage: Novel expression vectors that display cloned antigens on the virion surface", *Science*, vol. 228 (Jun. 1985): 1315-1317.

Tanaka et al., "In situ phage screening: A method for identification ofsubnanogram tissue components in situ", *The Journal of Biological Chemistry*, 277.33 (Aug. 2002): 30382-30387.

Tordsson et al., "Efficient selection of scFv antibody phage by adsorption to in situ expressed antigens in tissue sections", *Journal of Immunological Methods*, vol. 210 (1997): 11-23.

Winter et al., "Making antibodies by phage display technology", *Annual Review Immunology*, vol. 12 (1994): 433-55.

Yao et al., "Vascular Biology, Atherosclerosis and Endothelium Biology: Targeting pancreatic islets with phage display assisted by laser pressure catapult microdissection", *American Journal of Pathology*, 166.2 (Feb. 2005): 625-636.

\* cited by examiner

A

B

C

A

B

A

B

C

A

B

METHOD OF IDENTIFYING FETAL ANTIGENS OR CELL SURFACE MARKERS USING PHAGE DISPLAY TECHNOLOGY

REFERENCE TO RELATED APPLICATIONS

This U.S. continuation patent application claims priority of U.S. patent application Ser. No. 12/096,594, filed Jun. 6, 2008, which is a U.S. National Phase of International Patent Application Serial No. PCT/DK2006/000693, filed Dec. 7, 2006, which claims priority of Denmark Application Serial No. PA 2005 01745, filed Dec. 8, 2005, all of which are incorporated herein by reference in their entirety. All patent and non-patent references cited in the application, or in the present application, are also hereby incorporated by reference in their entirety.

FIELD OF INVENTION

The present invention relates to methods for detection and characterisation of cells, tissue or target antigenic material of very limited availability. The analysis of rare cells, such as foetal cells in a maternal blood sample or a micometastatic cell, is complicated by the low abundance of such cells and because the biological sample often will comprise a majority of other cells or tissue material besides the rare cell of interest. The possibility to analyse rare cells and other biological material of limited availability will permit the development of new diagnostic methods with a less invasive character.

BACKGROUND OF INVENTION

The examination of foetal cells for early detection of foetal diseases and genetic abnormalities is carried out in connection with many pregnancies, in particular when the maternal age is high (35 years or above) or where genetic diseases are known in the family. Foetal cells may be obtained by amniocentesis, the removal of amniotic fluid from the amniotic cavity within the amniotic sac or by chorion biopsy, where biopsies are taken from the placenta, so-called invasive sampling.

Prenatal aneuploidy screening employs either standard chromosome analysis or FISH analysis using specific DNA probes for the elucidation of numerical aberrations of chromosomes, particular chromosomes 13, 18, 21, X and Y in the foetus.

Due to the invasiveness of the methods described above and the risk of abortion associated herewith, it would be advantageously to perform foetal diagnosis by a non-invasive procedure, such as for example by use of a maternal blood sample.

During pregnancy a variety of cell types of foetal origin cross the placenta and circulate within maternal peripheral blood. The feasibility of using foetal cells in the maternal circulation for diagnostic purposes has been hindered by the fact that foetal cells are present in maternal blood in only very limited numbers, reported numbers have been from one foetal cell per $10^5$-$10^8$ nucleated maternal cells or 1-10 foetal cells per ml maternal blood.

In order to use foetal cell present in maternal blood for diagnostic purposes, methods suitable for isolation and/or identification of foetal cells are required.

Most foetal cells cannot be distinguished from maternal cells on the basis of morphology alone, thus alternative methods of identification of foetal cells have been investigated.

Foetal cells present in maternal blood include erythroblast, foetal leukocytes and trophoblast cells. Recently, foetal cells with stem cell properties have been indicated to be present in pregnant women and described as pregnancy-associated progenitor cells (PAPCs) and foetal mesenchymal stem cells (Khosrotehrani and Bianchi, 2005)

As described above different types of foetal cells, such as nucleated erythrocytes have be identified in maternal blood samples but so far, the efficiency of detecting these cells is very low. This may be due to the low number of foetal cells present in a maternal blood sample and/or due to the method employed for detection of said foetal cells.

Due to the very limited number of foetal cells in maternal blood separation or enrichment of the maternal blood sample with respect to the foetal cells is often conducted by for example negative selection, i.e. removal of maternal cells.

Maternal cells may be removed by density gradient centrifugation, by removing maternal cells with an antibody to a cell surface antigen or alternatively by lyses of maternal erythrocytes, optionally combined with immunologic methods for removing the maternal cells.

Alternatively foetal cells are separated from maternal cells by using flow cytometric methods or alternatively by a new technique, in which, a two-step enrichment procedure is performed to isolate trophoblast cells, consisting of a density gradient centrifugation and negative immunoaffinity isolation using Magnetic Activated Cell Sorter (MACS) Separation techniques and monoclonal antibodies or ligands specific to foetal cells.

It is however, a problem that due to the enrichment/separation procedures some of the foetal cells may also be removed leading to even fewer foetal cells in the blood sample to be analysed. Particular antibody selection methods may lead to a loss of foetal cells not expressing the antigen at a sufficient level.

Most methods are thus biased by the selection criteria of the enrichment/separation step. Two methods for unbiased quantification of total amount of foetal cells are available. Both methods are based on detection of Y-chromosome sequences. One is quantitative PCR, which is rather imprecise and the other is FISH staining of Y-chromosome in nuclei followed by counting. The enrichment step in the latter is based on initial carnoid fixation of whole blood, which dissolves all cell membranes thereby lysing the erythrocytes and removing the cytoplasm and many nucleoproteins of the nucleated blood cells. This treatment thus results in a nuclear pellet, which can be smeared onto slides. These slides are ideal for FISH-analysis, since the removal of so many proteins makes the nuclear Y-chromosome sequences easy assessable for the Y-chromosome specific probe. Both the PCR and FISH based techniques have been used to quantify total number of foetal cells and the most reliable reports all come to similar results, namely about two foetal cells pr. ml full blood. The problem with this quantification is however, that neither of the two methods allows identification or characterisation of the foetal cell disclosed. For the PCR-method due to only specific Y-chromosomes sequences being measured, and for the FISH-method due to the carnoid fixation removing all cytoplasm.

Immunocytochemical methods for detecting erythroblast, lymphoblast and trophoblast have been developed and blood from pregnant women investigated. In general very varying results have been obtained, some very compatible with the previous mentioned cell unspecific estimates. If however the foetal origin of a candidate cell is established without doubt (double and independent verifications) the general experience is, that the number of the three candidate cell types mentioned are one to two orders of magnitude lower than what was found by the cell unspecific methods. Thus the maternal blood may comprise foetal cells which are none of these three proposed cell types.

In general the methods described so far are laborious and complex and thus not suitable for routine analysis.

Thus improved methods for identification of foetal cells are required in order to utilise foetal cells circulating in pregnant women for non-invasive pre-natal diagnosis.

Usable tools in elucidating the identity of foetal cells are binding members such as antibodies or antibody fragments or alternative binding molecules capable of specifically recognising said foetal cells.

In general antibodies are generated by immunization of animals, preferably rodents. This usually requires a substantial amount of the antigenic material for sequential immunisation and/or several rounds of selection. These methods are thus not suitable when only a small amount of the antigenic material is available and when the antigenic material comprises multiple independent antigens. It is further normally accepted that a high purity of the target antigenic material is required to obtain suitable antibodies using these methods.

In some situations a binding member towards a minor fraction of molecules present in a sample is desired. That may be such as a specific cell type in a sample comprising multiple cell types. As purification of this minor fraction of molecules for which a binding member is thought is not feasible or otherwise undesired, alternative methods are required for generation of binding members towards target antigenic material present in a low ratio compared to the amount of non target antigenic material in a sample.

As described above the abundance of foetal cells in maternal blood is very limited and only available in small amounts and the ratio of foetal cells compared to maternal cells in maternal blood is less than 1/1000. In addition foetal cells are not easily purified from the maternal blood sample, as a substantial amount of the foetal cells may be lost during purification, thus conventional methods of generating antibodies are not efficient for the purpose of generating antibodies for recognition of foetal cells.

As described herein, the applicant has developed a method of identifying foetal cells furthermore said method allow the generation of binding members recognising said foetal cells. Hereby tools suitable for the development of prenatal diagnostic methods are made available.

It is further foreseen that the method of generating binding members may have a general application for generation of binding members recognising target antigenic material of limited availability or for the generation of binding members recognising target antigenic material present intermixed with non-target antigenic material in a sample.

SUMMARY OF THE INVENTION

It is an object of the present invention to provide for a method for detecting foetal cells in a maternal blood sample. The method developed by the inventors is cell type unspecific and enables detection of chromosomes, conservation of cell morphology and immunoassaying of cell type specific proteins.

Previous methods used for the identification of foetal cells in maternal blood samples were generally aimed at identifying foetal cells of a particular type by including an immunologic selection step selecting specific cell types expected to be present in the maternal blood sample. Foetal cells as trophoblasts, erythroblast (nucleated erythrocytes) and foetal leukocytes have been identified using such procedures. The method according to the present invention does not discriminate between different nucleated cell types and thus enables detection of foetal cells of various cell types. The identified cells may thus be any type of foetal nucleated blood cells, such as, but not limited to, leucocytes, stem cells (such as hematopoietic stem cells or mesenchymal stem cells) or placenta derived cells, such as trophoblast cells. The method according to the invention has further provided a method allowing detection of foetal cells of new cell types as the method is not limited to foetal cells of one or more particular cell types. Foetal cells of any cell type may be identified using the method described herein including foetal cells of cell types previously not seen, which may be such as a primitive stem cell.

The method described herein is based on the ability to analyze a large number of cells. As a consequence thereof, the need for strong enrichments procedures have disappeared and the risk of losing foetal cell present in the maternal blood sample is minimized. The method includes applying a mild fixation and permeabilisation step, which at the same time does not prevent accessibility for a hybridisation probes. The method according to the invention conserve protein content and cell morphology, the subcellular compartments of the cells, particular the cytoplasm and the nucleus.

An aspect of the present invention relates to a method of detecting a foetal cell in a maternal blood sample comprising the following steps:
a. providing a maternal blood sample,
b. fixing and permealizing nucleated cells present in said sample while;
    maintaining cell morphology,
    maintaining protein content of the cells and
    ensuring accessibility for a hybridisation probe and
c. adding a hybridisation probe
d. detecting at least one foetal cell.

Any suitable type of fixation and permeabilisation method may be used, such as for example methanol and/or acetone treatment.

The method may further comprise a pre-fixation step, whereby any fragile foetal cells are maintained, which preferably comprise a PFA treatment, most preferably the cells are pre-fixed in a solution comprising 0.1-4% PFA.

Following a re-fixation step may be used to provide further stability and sensibility of the sample during the hybridisation procedures. Such re-fixation step may comprise PFA treatment, such as incubation of the cells in a solution comprising 0.1-5% PFA. Following the samples are conveniently dehydrated in ethanol.

Thus in an embodiment the invention relates to a method of detecting a foetal cell in a maternal blood sample comprising the following steps;
a. providing a maternal blood sample,
b. pre-fixing
c. fixing and permealizing nucleated cells present in said sample while;
    maintaining cell morphology,
    maintaining protein content of the cells and
    ensuring accessibility for a hybridisation probe
d. re-fixing
e. adding a hybridisation probe and
f. detecting at least one foetal cell.

The number of maternal cells largely exceeds the number of foetal cells present in a maternal blood sample, thus it may be useful to include a step of enrichment whereby maternal cells are removed from the sample to be analysed. The enrichment step may be performed at any suitable time point during the procedure, most suitable as an initial step. In order not to remove any foetal cells it is preferred that the enrichment step does not discriminate between different foetal nucleated cell types. A large fraction of the maternal cells in the blood sample is comprised by erythrocytes. Several methods of removing erythrocytes is known, and most convenient is erythrocyte lysis, which may be achieved by $NH_4Cl$ mediated lysis.

As the method of detection of at least one foetal cell according to the invention includes a fixation and permeabilization step which ensures accessibility for a hybridization probe, the foetal cell may following be detected using a hybridisation technique, which may be used for detecting DNA or RNA within the nucleus and/or cytoplasm of the cells. Hybridization may be used for detection of chromosomal DNA or RNA molecules, such as mRNA. The present invention may for example be used for the detection of male foetal cells by used of FISH, which may be confirmed by reverse colour FISH.

In a further embodiment the methods of detection of at least one foetal cell according to the invention may include examination of morphological or epigenetic characteristics for identification of at least on foetal cell.

The method described further enables detection of a rare foetal cell, such as a cell present in a ratio of less than 1 to $10^3$ maternal nucleated cells. Thus the method provided herein enables examination of a large number of cells, which may be performed using an automated scanner system.

The method of the invention provides a novel approach to the analysis of a maternal blood samples and thus provides a new method for identification of foetal cells, and it follows that foetal cells identified using this method may be of a cell type different from foetal cells previously identified.

An aspect of the invention relates to a foetal cell identified by the method according to the invention.

The at least one foetal cell identified by the method according to the invention thus provides a new tool for generating foetal cell specific binding members, identification of foetal cell specific antigens and following the use of binding members and antigens in assays methods, for use in such as pre-natal diagnosis.

The at least one foetal cell identified by the method described herein are useful for generating foetal cell specific binding members, which may be obtained by any suitable method such as, but not limited to, phage display.

The present invention in an aspect relates to a method of isolating binding member, such as, but not limited to, antibodies or antibody fragments recognising antigenic material of limited availability, such as cells of a specific cell type or a small sub-populations of cells, such as foetal cells in a maternal blood sample.

It is envisioned that this method has a general application for the generation of binding members recognizing target antigenic material which is only available in very limited amounts. Antigenic material of limited availability may be such as a single cell either in a suspension of other cells of a different cell type or a specific cell in a heterogeneous tissue, e.g. a micrometastatic cell. or e.g. a single cell of a tumor. The method may further be applied to antigens present in a tissue sample, such antigens present in the extracellular matrix. Limited availability, further relates to the rareness of the antigenic material, i.e. the low ratio of the amount of target antigenic material compared to the amount of non target antigenic material, such as a ratio of less than 1 target cell to $10^3$ non-target cells.

An aspect of the invention relates to a method of isolating a binding member recognising target antigenic material of limited availability, comprising the steps:

a. identifying the target antigenic material,
b. contacting said antigenic material with a binding member generating system,
c. isolating binding members recognising the antigenic material.

In an embodiment the target antigenic material may be limited to only one cell.

Herein limited availability may refer to the rareness of the target antigenic material. In an embodiment the ratio of the target antigenic material compared to non-target antigenic material is less than 1/1000. In a preferred embodiment the ratio of the target antigenic material compared to non-target antigenic material is less than 1/10.000.

In a preferred embodiment the binding member generating system allows linking of the phenotype and the genotype of binding members generated by the system.

The method according to the invention may further comprise a step of minimizing isolation of binding members recognising non-antigenic material, as may be obtained by protection of the antigenic material and any genetic information encoding the binding member, bound thereto, from agents or treatment capable of rendering the genetic material non-replicable, such as UV irradiation.

The method according to the invention is useful for generation of binding members recognizing target antigenic material of limited availability, such as foetal cell as identified by the method described herein with out prior purification.

In an embodiment the method is for generating foetal cell specific binding members such as recombinant antibody fragments generated by use of phage display.

In addition the method of generating binding members according to the invention is not dependent on the specific identity of the antigen, e.g. isolated binding members may recognize different antigens available on/in the target antigenic materiel, e.g. the cell or tissue. The method further allows the generated binding members to be retested on the original target antigenic material whereby specificity may be confirmed.

Binding members obtained by the method according to the invention may subsequently be used for the identification of antigens recognized by the binding member.

An aspect of the invention relates to binding members specifically recognising foetal cells such as foetal cells identified by the method described herein. Such binding members may be used to identify foetal cell antigens, which may further be used for generating alternative binding members recognising said foetal cell antigen.

Binding members specifically recognising said foetal cell antigen, may be used in an assay method. Such methods may have various purposes, such as isolation of foetal cells from a maternal blood sample or for pre-natal diagnosis using a maternal blood sample.

An aspect of the invention relates to an assay method comprising the following steps;

a. providing a maternal blood sample,
b. selectively labelling at least one foetal cell by labelling of a foetal cell antigen according to the invention in said blood sample.

An aspect of the invention relates to an assay method comprising the following steps;

a. providing a maternal blood sample,
b. selectively labelling at least one foetal cell by use of a binding member according to the invention, in said blood sample.

Selectively labelling may be performed using an immunodetection technique, preferably by use of a binding member according to the invention.

The assay method may further comprise any of the steps described herein in relation to the method of detecting at least one foetal cell according to the invention.

Said selectively labelled foetal cell may be isolated from the sample, by used of any suitable method such as FACS analysis and MACS analysis.

In further embodiments said selectively labelled foetal cell may be subject to in situ chromosomal/DNA analysis, for the purpose of gender determination or for detection of chromosomal abnormality. This is preferably performed by a DNA hybridisation technique. Examples of such techniques includes, but is not limited to fluorescent in situ hybridization (FISH), primed in situ labelling (PRINS), quantitative FISH (Q-FISH) and multicolor-banding (MCB). Alternatively gender and/or chromosomal abnormality may be determined by a PCR technique.

Analysis of a maternal blood sample may be performed at any time during pregnancy, preferably at 4-24 weeks of gestation and more preferably at 6-15 weeks of gestation.

Isolated foetal cells may further be isolated in order to obtain a foetal cell population, such as a stem cell population, which may be used for treatment.

DESCRIPTION OF DRAWINGS

FIG. 1B is an enlarged panel of FIG. 1A, where the Y chromosome is marked by an orange label (arrow) and the X chromosome by a green label. In FIG. 1C the same cell was used for a second hybridization in which the color of the probes were exchanged, such that the Y chromosome is green (arrow) and the X chromosome orange. FIG. 1A is a picture of large field on the same slide after the second hybridization.

In FIG. 7B the same date is represented with the only difference being that the value for background binding to lymphocytes (lymp-blank) was subtracted from the K562-blank value before dividing by the lymp-blank value.

In FIG. 8B the binding of the same clones to lymphocytes is shown and in FIG. 8C the background binding is shown.

DETAILED DESCRIPTION OF THE INVENTION

Method of Detecting a Foetal Cell

Figure 1:
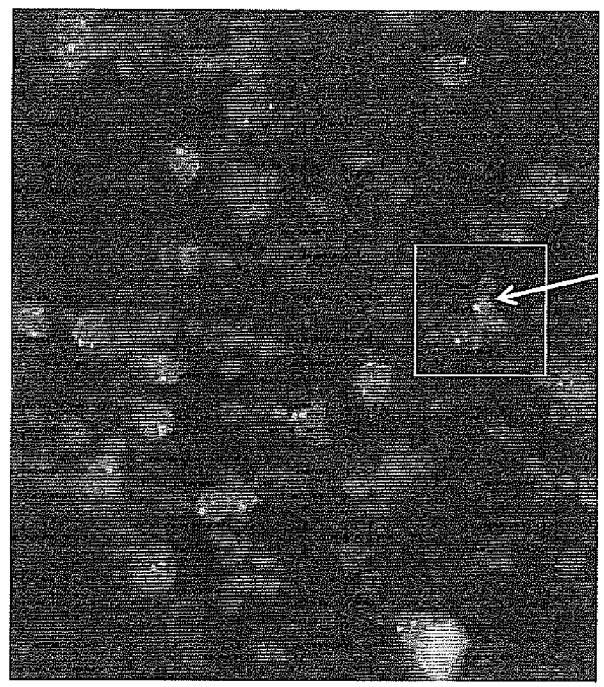
FIGS. 1A-1C show detection of one male foetal cell in a maternal blood sample by use of FISH. Detection was performed by FISH analysis, where probes hybridizing specifically to the X and Y chromosome were applied. Each probe was labeled with a unique fluorescent marker.
Figure 1:
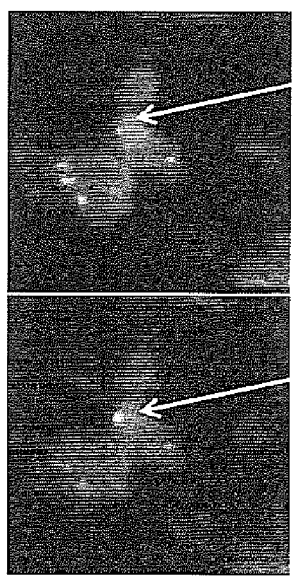

The present invention relates to a method of detecting a foetal cell in a maternal blood sample.

In order to detect foetal cells in the sample, the applicant has developed a suitable method for detection foetal cells in a sample, such a method may include FISH analysis or immunostaining. Detection of the Y chromosome may for example be used, for the detection of foetal cells from male embryos. Using a protocol as describe herein the inventors have detected foetal cells in maternal blood samples.

The steps of the method according to the invention is performed under mild condition suitable for maintaining the cell morphology i.e. the cytoplasm and nucleus of the cells, in particular the cytoplasm of foetal cells which may be more fragile than nucleated maternal cells. Maintaining the morphology of the cells requires that the cytoplasm and the nucleus may be clearly visualised in a microscopy following the fixation and permeabilization step. It is further preferred than the protein content is maintained by said fixation and permeabilization step, i.e. that cellular proteins expressed by the cell and in particular surface proteins expressed by the cells is conserved an available for recognition by a binding member, such as an antibody following fixation and permeabilization of said cell.

The protocol for detection of at least one foetal cell according to the invention enables detection of foetal cells, which based on morphological characters appears to be of a different cell type than foetal cells previously recognised in maternal blood.

Particularly, a male foetal cell was found to be of a different type than previously identified nucleated foetal cells, such as nucleated erythrocytes (erythroblasts), syncytiotrophoblasts and leukocytes described above. Thus the results suggest that a foetal cell of a previously unrecognised cell type is detected using the method according to the invention.

The detected foetal cell may be discriminated from cells previously detected in maternal blood samples by the morphology, extra- or intra-cellular markers. In an embodiment the foetal cell is discriminated from previously detected foetal cells by an enlarged cytoplasm and/or an irregular or elongated nucleus.

In an embodiment the invention relates to a method of detecting a foetal cell in a maternal blood sample comprising the following steps:
a. providing a maternal blood sample,
b. fixing and permealizing nucleated cells present in said sample while
   maintaining cell morphology,
   maintaining protein content of the cells and
   ensuring accessibility for a hybridisation probe
c. adding a hybridisation probe and
d. detecting at least one foetal cell.

Foetal cells may be distinguished from maternal cells by the specific recognition of a foetal cell antigen, such as by staining with a labelled antibody to a protein selectively produced by foetal cells. Alternatively foetal cells may be distinguished from maternal cells by the specific recognition of DNA or RNA encoding a protein selectively or substantially selectively produced by foetal cells. The foetal cell may further be distinguished from the maternal cells by epigenetic characteristics, such as telomere length or methylation status.

Alternatively, morphological characteristics may be used to distinguish foetal cells from maternally derived cells.

Detection of at least one foetal cell may include
detecting DNA in a foetal cell by hybridisation technique or
detecting RNA, particular mRNA, in a foetal cell by hybridisation technique or
detection of foetal cell antigen in/on a foetal cell.

The method steps described herein may further be used in combination with the assay method based on the foetal cell, foetal cell specific antigen and foetal cell specific antigen binding member described herein below.

Maternal Blood Sample

It is desirable to obtain as large a maternal blood sample as possible in order to increase the total number of foetal cells. However, due to practical problems the sample must be within certain limits. Accordingly, the size of the maternal blood sample is preferably in the range of 0.5 to 40 ml, such as in the range of 1 to 30 ml, such as from 2 to 20 ml or 3 to 10 ml.

The ratio of nucleated foetal cells in a maternal blood sample is a described in the background section very low, maybe as low as $1/10^7$, or even lower. The method according to the invention enables detection of at least one foetal cell in a maternal blood sample wherein the ratio of foetal cells to nucleated maternal cells is less than 1/100, such as preferably 1/1000 or such as more preferably 1/10.000. In specific embodiments the ratio of foetal cells to nucleated maternal cells is less than 1/50.000 or preferably less than 1/100.000, such as more preferred less than $1/10^6$, even more preferably less than $1/10^7$ or most preferably $1/10^8$.

Also, according to the invention the sample may be diluted or concentrated at anytime during the method of identification of the foetal cells (to facilitate the identification of the foetal cells). The sample may be diluted at least 1.5 times, such as twice, more preferred at least three times, such as five times by adding isotonic buffers, such as saline solutions, phosphate buffered saline solutions, PBS, and/or suitable growth media, such as basal media, and tissues growth media. The sample volume may be decreased to less than 80%, such as 70, or 60 or 50% of the original sample volume, or even preferable to less than 40%, such as 25% of the original sample volume.

The maternal blood sample provided is preferably obtained from a pregnant woman between 5-24 or 6-20 weeks of gestation, more preferably between 7-16, or 8-12 weeks of gestation.

Sedimentation

The cells present in the blood sample may be concentrated by sedimentation, where the majority of cells present in the sample is allowed to sediment. The blood sample may prior to sedimentation be diluted in a suitable solution, such as 0.15 M NaCl. The sedimentation may continue until sedimentation has occurred, such as for at least 5 hours, or over night (see example 1).

Preferably the sample is allowed to sediment at a temperature below room temperature, such as at a temperature of less than 15° C., such as less than 10° C. or 8° C. or 6° C., preferably at a temperature of 2-8° C. or around 4° C.

A minor population of cells with a low density may not sediment and may be isolated by mild pre-fixation as described below, such as in 0.5% paraformaldehyde followed by centrifugation as described in example 1.

Enrichment

According to the invention enrichment may be performed to increase the number of foetal cells relative to the number of maternal cells and/or an increase in the number of foetal cells relative to the current sample volume.

Methods of enrichment can include but is not limited to, density gradient centrifugation, FACS, MACS, whereby negative or positive selection of different cells may be accomplished. The enrichment procedure may involve multiple steps such as lyses of maternal cells followed by any suitable separation technique.

A preferred method of enrichment is lysis of erythrocytes such as $NH_4Cl$ mediated lysis, which allows selective lysis of erythrocytes leaving nucleated cells intact. Methods of $NH_4Cl$ mediated erythrocyte lysis is know by a person skilled in the art. A method of erythrocyte lysis is described in the example 1 herein. Preferably a concentration of 0.1-0.2 mM $NH_4Cl$ is used, such as 0.14-0.18 mM $NH_4Cl$ more preferably mM 0.15-0.17 $NH_4Cl$.

Pre-Fixation

The inventors have found that an improved result is achieved when cells are pre-fixed prior to mounting of the cells on a slide for further processing. Thus the application provides a method of detecting foetal cells in a maternal blood sample comprising a step of pre-fixation, such pre-fixation may involve a mild paraformaldehyde treatment, such as incubation of cells in a solution comprising 0-5% PFA, 0.1-4% PFA, preferably 0.2-1% or 0.2-0.7% PFA, most preferably 0.4-0.6 or about 0.5% PFA. Pre-fixation may be performed for such as at least 1 minute, 2 minutes, 4 minutes or 6 minutes, or such as 10 minutes. In specific embodiments pre-fixation may be performed for up to 24 hours, although preferably for less than 12 hours, such as 8, 4 or 2 hours, more preferably less than 1 hour, or less than 30 minutes, such as 20 or 15 minute, most preferably for less than 10 minutes, such as for about, 8, 6, 4 or 2 minutes.

Detection

According to the method of the invention the foetal cell may be detected using various suitable techniques. In order to detect the foetal cell the foetal cells are selectively labelled. The selective labelling of the foetal cells may be carried out by any suitable method as described herein distinguishing foetal cells from maternal cells by the specific recognition of a foetal cell antigen or a protein selectively produced by foetal cells or by the specific recognition of DNA or RNA encoding a protein selectively or substantially selectively produced by foetal cells. Alternatively foetal cells may be detected based on epigenetic characteristics as described above.

Hybridisation Techniques

Accordingly, it is an object of the present invention to provide for the selective labelling of foetal blood cells in the maternal blood sample based on a hybridisation technique. Male foetal cells may be detected using a probe to male specific mRNA or male specific chromosomal DNA. Alternatively, probes recognising m-RNA selectively expressed by foetal cells may be used.

Foetal cell specific RNA, generally messenger RNA (mRNA) sequences may be used as foetal cell markers. The presence of such mRNA indicates that the gene for the foetal protein is being transcribed and expressed. The probes used to identify foetal cells in a sample containing foetal and maternal cells include nucleic acid molecules, which comprise the nucleotide sequence complementary to the nucleotide sequence of the RNA molecule encoding a specific protein. Foetal cells contain distinct mRNAs or RNA species that do not occur in other cell types. The detection of these RNAs, can serve to identify cells of foetal or embryonic origin.

As described below foetal cell antigens and mRNA encoding these antigens may be detected in a foetal cell although such methods have so far not resulted in satisfactory results, which may be due to the lack of suitable foetal cell markers.

Probe

According to the invention the probe may be any type of probe known in the art for detection of RNA or DNA molecules. Conventional probes know by a person skilled in the art comprise, RNA and DNA probes synthesised from nucleotides of deoxynucleotide, respectively using a commercial synthesiser. Probes may be comprised of the natural nucleotide bases or known analogues of the natural nucleotide bases. It is further contemplated that the probes may be oligomers comprising one or more nucleotide analogs including peptide nucleic acids and other synthetic molecules capable of Watson Crick-base pairing.

For detection of chromosomal DNA Fluorescence In Situ Hybridization (FISH) is frequently employed. One procedure for performing X-Y FISH is described in example 2. Male specific chromosomal. DNA or RNA may be detected by similar means. As an initial procedure the method of detection a foetal cell according to the invention was aimed at identifying male cells present in the maternal blood sample, whereby identification of a foetal cell is achieved.

Automated Scanning

Since the preparation of cell according to the invention involves only limited enrichment of foetal cells and embodiment of the invention relates to the detection of the very rare foetal cells by automated scanning using commercial scanners at high speed. These scanners are in principle fluorescence microscopes with a moving stage and a camera. The whole slide is photographed in sections and each picture analysed for presence of foetal cell specific signals i.e. Y-chromosome signals. Specialized software that can precisely define a foetal cell as such under the preparative conditions employed is used. The parameters developed in the software are size and intensity of signal and shape, density and size of nucleus.

Identification of Male Foetal Cell

In an embodiment of the invention a male foetal cells is detected using a chromosome Y specific probe. Such labelling methods are well know to persons skilled in the art and are thus only briefly described below. A male foetal cell may further be detected by HLA typing for the paternal isotypes.

Detection of male foetal cells has been used as an example herein as any male cell detected in a maternal blood sample is considered to be of foetal origin.

The method described herein (example 1 and 2) was employed for the identification of a male foetal cell (FIG. 1). The method is based on a method of fixation traditionally used for conserving proteins, which at the same time insures that FISH probes have access to the nucleus. The pre-fixation is followed by additional fixation and permeabilization steps. By use of this method, followed by reverse colour FISH, a male foetal cell was identified in a maternal blood sample from a woman pregnant with a male foetus. The method of fixation conserving cellular proteins, allows further analysis of the detected cells and thus the identification of cell type specific proteins as is described herein. This method of identification of foetal cells may thus lead to the identification of novel foetal cell types. FIG. 1 shows one male foetal cell identified by the method according to the invention (for protocol see example 2). FIG. 1A shows a field of vision wherein one spectrum green labelled cell is identified, while the remaining nucleated cells are labelled with spectrum orange. FIGS. 1B and 1C show enlargements of the area containing the male foetal cell from the first and second hybridization, respectively. The labelling with spectrum green and spectrum orange has switched from B to C, confirming that the cell is a true foetal cell. The FISH labelling of the male foetal cell is indicated by an arrow.

The cell is characterized by an irregular and/or elongated nucleus and a large cytoplasm. Such morphology is not consistent with the morphology of foetal cell previously identified in maternal blood samples and thus a new foetal cell type may have been identified, for example a stem cell.

The new approach described herein for detection of at least one foetal cell, has enable identification of a foetal cell with characteristics different from previously identified foetal cells, indicating that a new type of foetal cell is identified. Such new foetal cell is useful for the generation of new foetal cell specific antibodies and identification of new foetal cell antigens.

It is furthermore possible to identify foetal cell specific morphological characteristics by characterisation of said identified foetal cell.

Foetal Cell Antigen

Foetal cell specific antigens are proteins or other macromolecules, including modifications of said protein or macromolecules selectively produced by foetal cells. Proteins which are foetal cell specific antigens are e.g. embryonic hemoglobin, such as E globin chains. Foetal cell specific antigens may be used for detection of foetal cells. Detection of male specific antigen may likewise be employed for the detection of male foetal cells.

Surface antigens are suitable for enrichment procedures by enabling labelling of foetal cells using conventional methods, whereby foetal cells may be isolated using FACS. Cellular antigens may likewise be used in an enrichment procedure although improved methods of using FACS may be required.

In a preferred embodiment a foetal cell antigen is a surface antigen.

The present invention provides a method of identification of a foetal cell with in a sample of maternal blood comprising a majority of non-foetal cells. The identified foetal cell is according to the invention used for identification of new foetal antigens or foetal cell markers. Screening of binding members for reactivity towards the identified foetal cells may lead to the identification of new foetal cell specific binding members and antigens as described herein below and in example 3 and 4.

Binding Members

A binding member according to the invention is any type of molecule, such as the molecules defined here below, capable of binding to a ligand, i.e. the target antigenic material or antigen as described herein.

The binding member may be a single moiety, e.g., a polypeptide or protein, or it may include two or more moieties, e.g., a pair of polypeptides such as a pair of single chain antibody domains. Methods of generating antibodies are well know to person skilled in the art, by immunisation strategies for the generation of monoclonal or polyclonal antibodies or in vitro methods for generating alternative binding members. Polyclonal antibodies may be such as sheep, goat, rabbit or rat polyclonal antibody. In addition any suitable molecule capable of high affinity binding may be used including antibody fragments such as single chain antibodies (scFv), particularly, Fab and scFv antibodies which may be obtained by phage-display (see below) or single domain antibodies (VHH) or chimeric antibodies. The binding member may be derived from a naturally occurring protein or polypeptide; it may be designed de novo, or it may be selected from a library. For example, the binding member may be or be derived from an antibody, a single chain antibody (scFv), a single domain antibody (VHH), a lipocalin, a single chain MHC molecule, an Anticalin™ (Pieris), an Affibody™, a nanobody (Ablynx) or a Trinectin™ (Phylos). Thus methods of generating binding members of various types are well known in the art.

Antibodies

A binding member may according to the invention be an antibody, such as any suitable antibody known in the art including other immunologically active fragments of antibodies or single chain antibodies. Antibody molecules are typically Y-shaped molecules whose basic unit consist of four polypeptides, two identical heavy chains and two identical light chains, which are covalently linked together by disulfide bonds. Each of these chains is folded in discrete domains. The C-terminal regions of both heavy and light chains are conserved in sequence and are called the constant regions, also known as C-domains. The N-terminal regions, also known as V-domains, are variable in sequence and are responsible for the antibody specificity. The antibody specifically recognizes and binds to an antigen mainly through six short complementarity-determining regions located in their V-domains.

Antibody Fragments

In one embodiment of the invention the binding member is a fragment of an antibody, preferably an antigen binding fragment or a variable region. Examples of antibody fragments useful with the present invention include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of cross-linking antigen, and a residual other fragment (which is termed pFc').

Additional fragments can include diabodies, linear antibodies, single-chain antibody molecules, and multispecific antibodies formed from antibody fragments.

The antibody fragments Fab, Fv and scFv differ from whole antibodies in that the antibody fragments carry only a single antigen-binding site. Recombinant fragments with two binding sites have been made in several ways, for example, by chemical cross-linking of cysteine residues introduced at the C-terminus of the VH of an Fv (Cumber et al., 1992), or at the C-terminus of the VL of an scFv (Pack and Pluckthun, 1992), or through the hinge cysteine residues of Fab's (Carter et al., 1992).

Preferred antibody fragments retain some or essential all the ability of an antibody to selectively binding with its antigen or receptor. Some preferred fragments are defined as follows:

Fab is the fragment that contains a monovalent antigen-binding fragment of an antibody molecule. A Fab fragment can be produced by digestion of whole antibody with the enzyme papain to yield an intact light chain and a portion of one heavy chain.

Fab' is the fragment of an antibody molecule and can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(Fab')$_2$ is the fragment of an antibody that can be obtained by treating whole antibody with the enzyme pepsin without subsequent reduction. F(ab')$_2$ is a dimer of two Fab' fragments held together by two disulfide bonds.

Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

In one embodiment of the present invention the antibody is a single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the $V_H$ and VL domains that enables the sFv to form the desired structure for antigen binding.

The antibody fragments according to the invention may be produced in any suitable manner known to the person skilled in the art. Several microbial expression systems have already been developed for producing active antibody fragments, e.g. the production of Fab in various hosts, such as *E. coli*, yeast, and the filamentous fungus *Trichoderma reesei* are known in the art. The recombinant protein yields in these alternative systems can be relatively high (1-2 g/l for Fab secreted to the periplasmic space of *E. coli* in high cell density fermentation or at a lower level, e.g. about 0.1 mg/l for Fab in yeast in fermenters, and 150 mg/l for a fusion protein CBHI-Fab and 1 mg/l for Fab in *Trichoderma* in fermenters and such production is very cheap compared to whole antibody production in mammalian cells (hybridoma, myeloma, CHO).

The fragments can be produced as Fab's or as Fv's, but additionally it has been shown that a VH and a VL can be genetically linked in either order by a flexible polypeptide linker, which combination is known as an scFv.

Natural Single Domain Antibodies

Heavy-chain antibodies (HCAbs) are naturally produced by camelids (camels, dromedaries and llamas). HCAbs are homodimers of heavy chains only, devoid of light chains and the first constant domain (Hamers-Casterman et al., 1993). The possibility to immunise these animals allows for the cloning, selection and production of an antigen binding unit consisting of a single-domain only. Furthermore these minimal-sized antigen binding fragments are well expressed in bacteria, interact with the antigen with high affinity and are very stable.

New or Nurse Shark Antigen Receptor (NAR) protein exists as a dimer of two heavy chains with no associated light chains. Each chain is composed of one variable (V) and five constant domains. The NAR proteins constitute a single immunoglobulin variable-like domain (Greenberg et al) which is much lighter than an antibody molecule.

According to the invention natural single domain antibodies may be considered an antibody fragment. The proteins may be produced and purified by any suitable method know by a person skilled in the art as described above.

In a further embodiment the binding member is active fragments of antibodies selected from Fab, Fab', F(ab)$_2$, Fv, HCAbs and NARs.

Non-Immonoglobulin Binding Members

In one preferred embodiment, the present invention relates to binding members derived from a naturally occurring protein or polypeptide; said protein or polypeptide may for example be designed de novo, or may be selected from a library. The binding member may be a single moiety, e.g., a polypeptide or protein domain, or it may include two or more moieties, e.g., a pair of polypeptides such as a pair polypeptides. The binding member may for example, but exclusively, be a lipocalin, a single chain MHC molecule, an Anticalin™ (Pieris), an Affibody™, or a Trinectin™ (Phylos), Nanobodies (Ablynx). The binding member may be selected or designed by recombinant methods known by people well known in the art.

In another embodiment of the invention the binding member is an affibody, such as any suitable affibody known in the art, in particular antibodies as defined herein, such as affibodies or immonologically fragments of affibodies. Affibodies are selected in vitro, from an affibody library constructed by combinatorial variation of the IgG binding domain of Protein A. Protein A is a surface protein from the bacterium *Staphylococcus aureus*. The biding domain consists of 58 residue, where of 13 are randomized to generate Affibody® libraries Thus, the size of an affibody is considerably less than of an antibody (www.affibody.com).

Method of Generating Binding Members

As described above foetal cells, obtained from a maternal blood sample, are of very limited availability and are not usable for immunization or other standard methods of generating binding members. The applicants have developed a method that allows generation of binding members recognising target antigenic material of limited availability and purity. The limited availability of the target antigen material may be due to the target antigen material being present in a sample intermixed with non-target antigenic material. In situations where purification of the target antigen material is not desirable or feasible alternative methods of providing specific binding members are required. The method described herein is thus not limited to the isolation and generation of binding members recognising foetal cells, but applies equally to other target antigen material of limited availability.

An aspect of the invention relates to a method of isolating binding members recognizing target antigenic material of limited availability comprises the steps:

a. identifying the target antigenic material,
b. contacting said target antigenic material with a binding member generating system and
c. isolating binding member(s) recognising the target antigenic material.

Target Antigenic Material

The target antigenic material may be any type of material for which specific binding members are thought. The method allows selection of binding members to non purified antigens or non-homogeneous antigens, the target antigenic material may be such as a mixture of antigens, cells or other material comprising multiple antigens.

In an embodiment the ratio of the amount of target antigen material compared to the amount of non-target antigen material is less than 1/100, such as less 1/5000, such as less 1/10,000 or preferably less than 1/50,000 or more preferably less than 1/100,000, such as less than $1/10^6$, more preferably less than $1/10^7$ or most preferably $1/10^8$.

The target antigen ratio, $$R_{TA} = \frac{\text{target antigen material}}{\text{non-target antigen material}}.$$

In an embodiment $T_{TA}$ is less than $1/10^2$, or preferably less than $1/10^3$, or more preferably less than $1/10^5$, even further preferred less than $1/10^6$, more preferably less than $1/10^7$ or most preferably $1/10^8$.

Depending on the type of antigen material the amounts may be calculated in numbers, weight or other suitable units.

In an embodiment the target antigenic material is a sample of cells, such as cells of a specific cell type for which binding members are thought. In an embodiment the target antigenic material may be limited to only one cell in a sample, where such a cell may be present either in suspension or fixed to a slide intermixed with other cells.

In an embodiment the target antigenic material is present on a slide, such as cells fixed on a slide. Said cell may be located on a slide in between other cells. Location of the cell may be available using micro-dissection/micro manipulation systems.

In a preferred embodiment the target antigenic material is one or more foetal cell(s), such as foetal cells identified according to the method described herein.

In a preferred embodiment the target antigenic material is a foetal cell identified as described herein. In a preferred embodiment the foetal cells is such as a male foetal cell identified by reverse colour FISH and automated scanning.

In an embodiment the target antigenic material is extracelluar matrix.

In an embodiment the binding member is selected from the group of antibodies, antibody fragments and non-immune binding members.

In a specific embodiment the binding member is an antibody. In a further embodiment the binding member is an antibody fragment. In a subsequent embodiment the binding member is a non-immune binding member.

Binding Member Generating System

The target antigenic material is contacted with any suitable binding member generating system known in the art.

The binding member generating system preferably allows a linkage between the genotype of the binding member and the phenotype of the binding member. Such linkage allows convenient characterisation of the sequence of an identified binding member. Such binding member generating system known in the art, include but are not limited to, ribosome display (Hanes, J et al and Lipovsek, D et al), mRNA display (reviewed in Gold, L (2001), DNA display (including cis display (Odegrip R et al, 2004)), yeast display (Boder, E T., et al. 1997), bacterial display (Francisco, J. A. et al, 1993 and Georgiu G et al 1997), retroviral display (Ager S, 1996, Buckholtz et al, 1998) etc. and phage display as described here below. The linkage of the genotype and phenotype provides easy access to the genetic information related to any identified binding member, whereby the region of specificity may be easily characterised.

The linkage between the phenotype and the genotype permit manipulation of the genetic material encoding isolated binding members.

In an embodiment the binding member generating system allows linkage between the genotype and the phenotype of binding members generated by the system In a preferred embodiment the invention relates to a method of isolating binding members recognizing target antigenic material of limited availability comprising the steps:

a. identifying the target antigenic material,
b. contacting said target antigenic material with a binding member generating system which allows linkage between the genotype and the phenotype of generated binding members and
c. isolating binding member(s) recognising the target antigenic material.

In a preferred embodiment the binding member generating system is based on phages expressing suitable binding members, such as antibody fragments on there surface as described here below.

Alternative methods such as compartmentalisation of genotype and phenotype may also be applied if the target antigenic material is analysed in suspension.

Binding Members Generated by Phage Display

Phage display technology (Smith et al, 1985, Winter et al, 1994 and Griffiths et al., 1994) is a useful system for generating binding member according to the invention.

Phage-displayed antibody technology enables generation of high-affinity binding sites without the constraint imposed by classical method for generating either polyclonal or monoclonal antibody. Phage libraries that are successfully used to generate desired binding sites are constructed from the genetic material obtained from human or other eukaryotic species. Various types of library formats are known to the person skilled in the art, such as but not limited to immunised libraries, naive libraries, semisynthetic libraries, single scaffold or single domain libraries. These libraries can for example, but not limited to, be generated from the light-chain and heavy-chain IgM-V-gene pools of B cells of non-immunized healthy donors, which are isolated from peripheral blood lymphocytes, bone marrow, or spleen cells. The antibody can also be engineered with in-built features that suit various downstream applications. The whole antibodies cannot be functionally expressed in bacteria, thus only the antibody fragments that contain the binding regions are displayed on the surface of the bacteriophage. It has been shown that both Fab and single-chain Fv (scFv) can be expressed on the surface of M13 without apparent loss of the antibody's specificity and affinity. Most of the phage libraries that have been constructed, display the antibody fragment on the surface of the phage minor coat proteins (pIII). Antibodies with an affinity in the 1-200 nM range are routinely selected. The affinity of the antibodies isolated from phage library can be further improved by various methods of affinity maturation.

In a preferred embodiment the binding member is an antibody fragment generated by phage display.

Isolation of Binding Members Recognising the Target Antigenic Material

Following the initial contacting of the target antigenic material and the binding member generating system, binding members associated with the target antigenic material are isolated and binding members recognising the target antigenic material are thereby obtained. Due to the linkage between the gene encoding the binding member and the binding member, the genetic information (the sequence) of the binding member is obtained at the same time. Binding members may be subjected to further rounds of selection in order to obtained binding members with high specificity. Steps of protein evolution/maturation may further be included in order to obtain binding members with a high affinity.

If the target antigenic material is not isolated from non-target antigenic material, the isolation of specific binding members may be more challenging as binding members associated with non-target antigenic material are preferably removed, inactivated and/or eliminated before isolating binding members bound to the target antigenic material.

By removing, inactivating and/or eliminating binding members associated with non-target antigenic material a higher proportion of antigen specific binding members specifically recognising the target antigenic material, compared to binding members recognising the non-target antigenic material is obtained.

The method of the present invention may further comprise a step of minimizing the number of binding members retrieved recognizing any non-target antigenic material present adjacent to the target antigenic material. This step serves to narrow down the number of binding members recognising non-target antigenic material which may be such as proteins or other macromolecules which are expressed at identical level in target antigenic material and in non-target antigenic material. In an embodiment the binding member generating system binding non-target antigenic material is inactivated.

As described above the binding activity and the genetic information of a binding member is preferably linked in the binding member generating system. The genetic material encoding the binding members may thus be compromised by introducing damage or crosslinks, where by the genetic information is rendered non-replicable. Such damage or crosslinks can be generated by various means known to a person skilled in the art, such as by UV irradiation.

In a preferred embodiment the minimizing step comprise UV irradiation.

It is evident that target antigenic material, including associated binding members must be protected from agents damaging the genetic information, such as UV irradiation. In an embodiment the target antigenic material and associated binding members is protected from UV irradiation by shielding. This is particularly useful when the binding members are linked to genetic/sequence information responsible for further replication or amplification of the binding member. During UV irradiation the target antigenic material is protected from UV irradiation by shielding the selected area. Binding members bound to the target antigenic material may be retrieved without contamination of binding members bound to material outside the protected region and these binding members may then be amplified by suitable methods.

Figure 2:
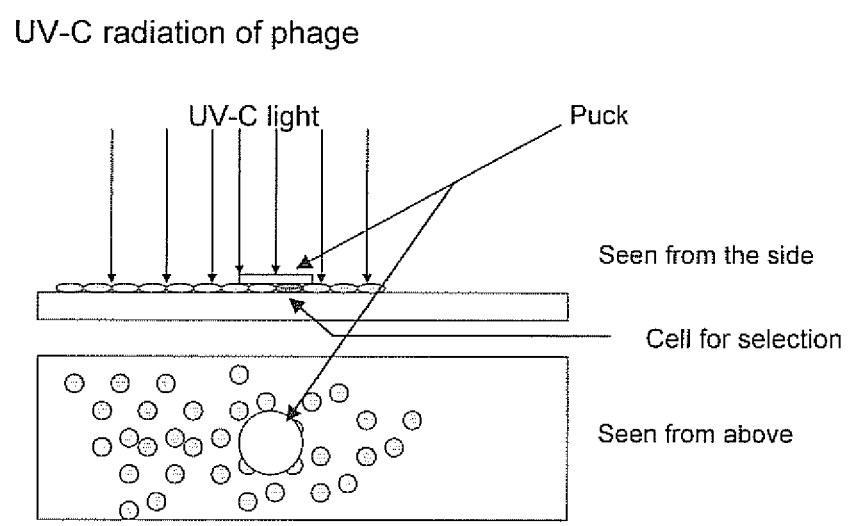
FIG. 2. Shielding using a puck.
Figure 3:
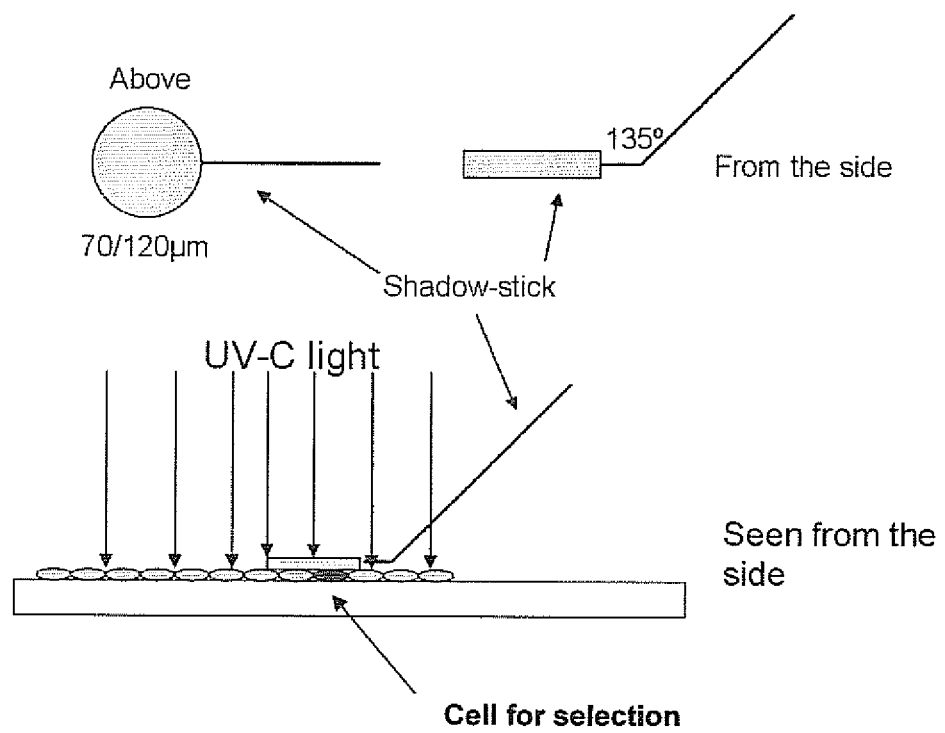
FIG. 3. Shielding using a shadow stick.

The shield may be any suitable particle or item capable of preventing UV light from reaching the selected region. Suitable shields may be shadow stick, gold plate or gold puck, which is to be position above the selected region during UV light exposure (FIG. 2 and FIG. 3).

The size of the shield may be such as 50, μm, 80 μm, 100 μm, 120 μm, 150 μm or 200 μm depending on the size of the selected region, preferably between 60 μm and 200 μm, more preferably between 70-120 μm.

Figure 4:
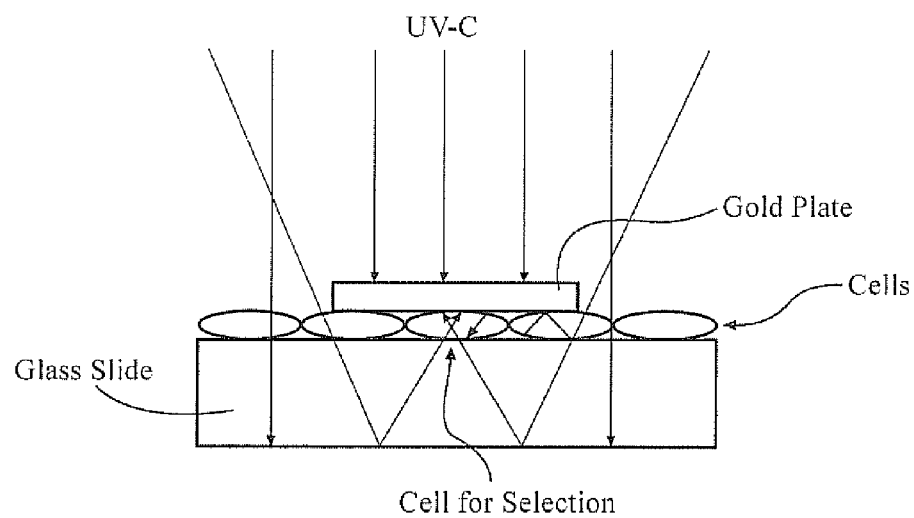
FIG. 4. Illustration of UV reflection.

In order to optimize the selection of binding members recognizing the target antigenic material in the selected region, reflection of the UV light may be minimized, to avoid inactivation of phages bound in the selected region. The problem of reflection is illustrated in FIG. 4.

Figure 5:
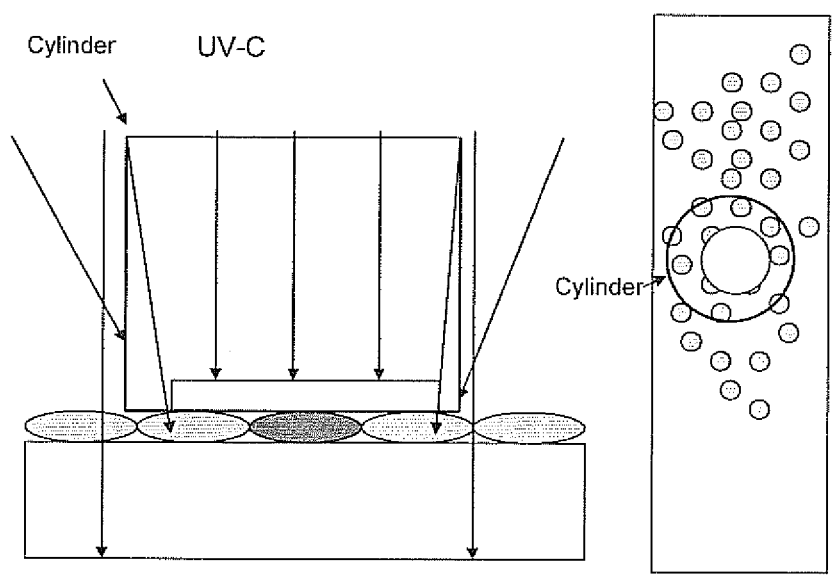
FIG. 5. Prevention of UV reflection using a cylinder.

UV reflection may be limited by reducing the light with non-vertical angel, by placing the shield close to the selected area, such as with in 5 mm, 3 mm, 2 mm and 1 mm. Reflection may further be decrease by a black back colour of the slide, or by grinding of the back surface. Alternatively a cylindrical wall may be placed around the selected area to prevent non-vertical UV light to reach the selected area from the side (FIG. 5).

Isolation of Binding Members

The step(s) of isolating binding members are dependent on the binding member generating system applied, and are thus selected accordingly.

In a particular embodiment, as described in example 8, binding members are generated by use of phages. Phages, expressing binding members, binding the target antigenic material may be isolated by eluting the phages from the selected area by use of any suitable method including such as by use of trypsin or in low pH buffer followed by neutralisation such as by use of mM Glycine, pH 2,2 and Tris-HCl for neutralization.

Following, the binding members are subcloned into a suitable vector for large scale production of the binding members. For binding members generated by used of phages this may conveniently be performed without the binding members being displayed on phage particles. Likewise for other methods, the availability of the genetic information may ease subsequent steps of selection.

The specificity of isolated binding members may then be tested against target antigenic material and non target antigenic material. Cell type specific binding members may be tested against cells of the same type and cells of a different type whereby cell type specific binding members may be identified.

In order to obtain foetal cell specific binding members the isolated binding members must be screen for reactivity towards non-foetal cells, such as adult blood cells particularly maternal blood cells.

Figure 6:
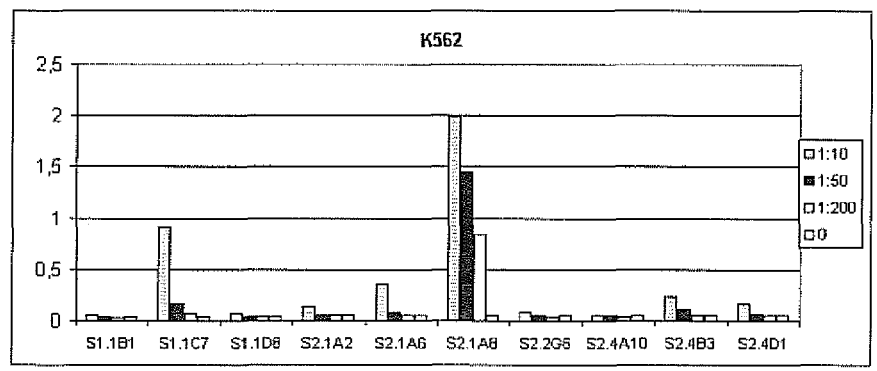
FIG. 6. Graphic illustration of ELISA assay tests of 10 selected antibody phage clones. A shows the binding to K564 cells, B and C show the control experiments using lymphocytes coated plates and blank plates, respectively.
Figure 6:
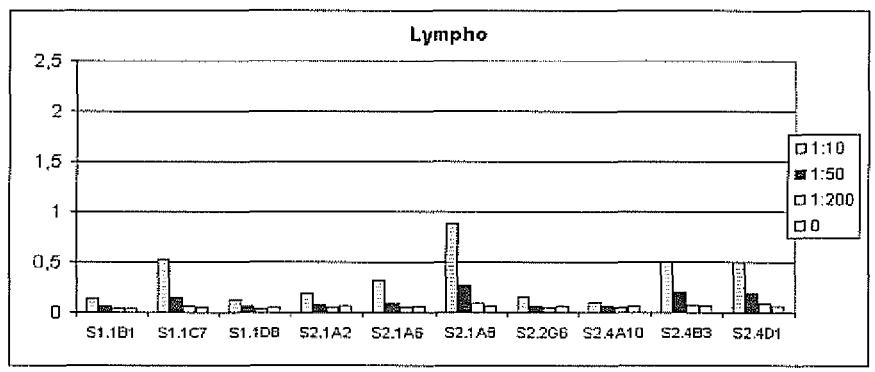
Figure 6:
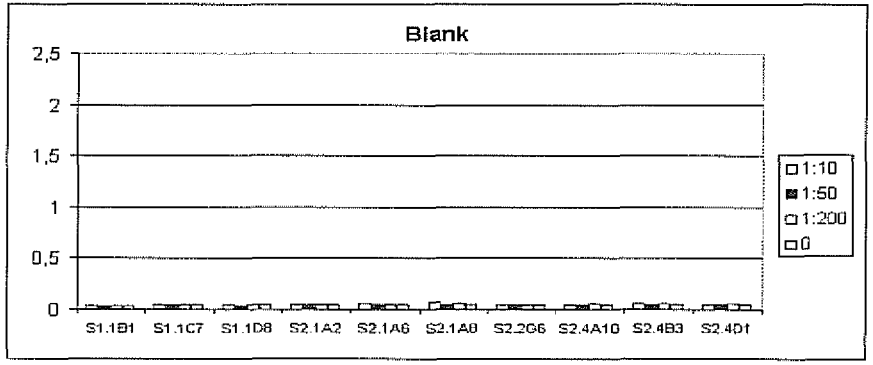
Figure 9:
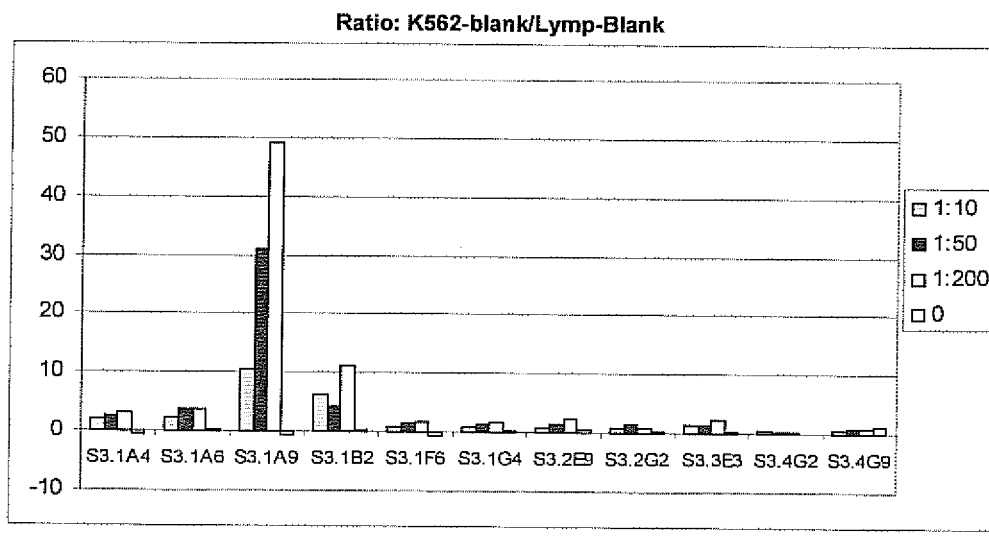
FIG. 9 shows the same experiment as shown in FIG. 7, with the 11 new recombinant antibodies for which the primary data is shown in FIG. 8.
Figure 9:
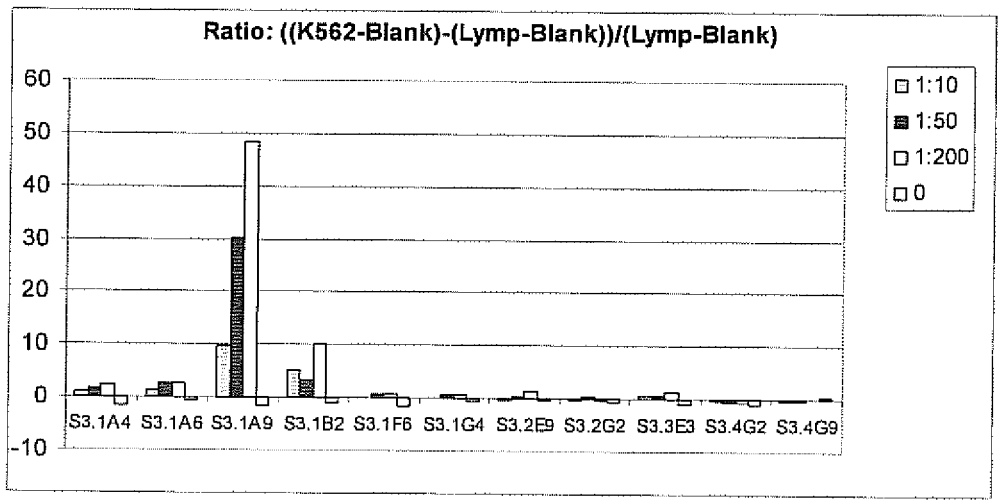

Binding members recognizing antigens present at similar or higher levels on adult blood cells, compared to foetal cells are to be excluded. This can be performed by staining a slide containing a mixed population of cells (such as the one use initial for selection of the binding members) or in an ELISA assay. The antibodies may be tested in ELISA against different cell types. As many different cultures as possible may be used, preferably including embryonic, foetal and stem cells cultures. Any cell line or cell lines similar or related to the identified foetal cell based on morphology may be preferred. Identification of a pattern of recognition may serve to validate the specificity of the isolated antibodies or antibody fragments In example 8, generation of phage antibody fragments to K562 cells is described. The specificity of the antibody fragments is evaluated by comparing the binding activity towards K562 cells to the binding activity towards lymphocytes (FIGS. 6, 9). The data shows that the method of the present invention is useful for generation of cell type specific antibody fragments, based on a very limited amount of target antigenic material, e.g few cells on a slide. The graphs shows examples of an antibody fragment (S2.1A8) with approximately 20 fold higher activity and an antibody fragment (S3.1A9) with approximately 48 fold higher activity at a dilution of 1:200, towards K562 cells than towards lymphocytes. As seen phage display is particular useful for generation of cell type specific antibody fragments.

According to the invention foetal cell specific binding member may be generated using identified foetal cells as antigen in the method described herein and in example 3 and 8.

The identified binding members such as scFv antibody fragments may be used for staining of foetal blood samples whereby the specificity and localization of the antigen is tested. The method described herein further allows retesting on the identified antibodies on the slide by re-hybridization procedures.

The binding members preferably bind specifically to a foetal cell antigen present on/in a foetal cell. As the method of identification of foetal cell and following the method of isolating binding members as described herein, are cell type unspecific, antibodies towards foetal cell antigens identified using these methods are cell type non-specific.

Accordingly, an aspect of the present invention relates to foetal cell specific binding members isolated by its binding capability to a foetal cell, such as a foetal cell identified as described herein. Binding members isolated by phage display are further preferred.

Identification of New Foetal Cell Specific Antigens

In order to obtain binding members specific for the foetal cell identified according to the method described herein the binding members are screened for cross reactivity with other cells and antigens. The specificity of the antibody is tested against a panel of previously known foetal cell markers to confirm the identification of binding members recognising a previously unknown foetal cell antigen/marker. Due to the initial detection method which does now discriminate between different cell types, the identified binding members may recognise a plurality of foetal cell types, even foetal cell types not previously known.

The binding members are screened against adult blood cells and/or previously know foetal cell makers, thus the binding members do preferably not bind foetal cell antigens such as embryonic hemoglobin, such as $\epsilon$ globin chains and zeta globin chains, and foetal hemoglobin, such as gamma globin chains and trophoblast specific antigens.

When specificity of the antibody is confirmed, the identity of the foetal cell marker/antigen recognised by the identified foetal cell specific antibody fragments may be determined. Antigens bound/recognised by the selected antibody may be identified by several methods (see example 5) know by the skilled person such as screening of c-DNA expression libraries or proteins purification procedures, examples of such methods include, but is not limited to, immunoprecipitation or 2D-PAGE followed by mass spectroscopy.

The identified foetal cell antigen may then be used to select further binding members specifically recognising said antigen, which may be used for labelling of foetal cells in maternal blood samples.

An aspect of the present invention relates to binding members, such as antibodies or antibody fragments recognising foetal cell antigens identified by the method described herein, such as by characterisation of antigens recognised by antibody fragments isolated by bio-panning of a phage display library on a detected foetal cell. Following such binding members, antibody or antibody fragments may be used for labelling of foetal cells.

The labelling as described below may be carried out by use of any specific binding member. Particular by use of an antibody selected from monoclonal and polyclonal antibodies or phage display generated antibody fragments. The binding members may be unlabelled antibodies, biotin labelled antibodies, fluorochrome labelled antibodies or both fluorochrome and biotin labelled antibodies recognizing any foetal specific antigen as identified by the method of the present invention.

Fluorochrome

The fluorochrome is selected to be excited in the wavelength area of the detection means, and furthermore in suitable combination with an optional second labelling. In particular the fluorochromes may be selected from FITC (fluorescein-isofluocyanate) or TRITC (Rhodanine Tetramethyl-isofluocyanate) having excitation at 495 nm and 520-530 nm, respectively. Further fluorochromes which may be used are listed in table 1.

TABLE 1

Wave length of excitation and emission of various flourochromes.

| Fluorochome | Ex (nm) | Em (nm) | MW | Notes |
|---|---|---|---|---|
| Reactive and conjugated probes | | | | |
| Hydroxycoumarin | 325 | 386 | 331 | Succinimidyl ester |
| Aminocoumarin | 350 | 445 | 330 | Succinimidyl ester |
| Methoxycoumarin | 360 | 410 | 317 | Succinimidyl ester |
| Cascade Blue | 375; 400 | 423 | 596 | Hydrazide |
| Lucifer yellow | 425 | 528 | | |
| NBD | 466 | 539 | 294 | NBD-X |
| R-Phycoerythrin (PE) | 480; 565 | 578 | 240 | |
| PE-Cy5 conjugates | 480; 565; 650 | 670 | | aka Cychrome, R670, Tri-Color, Quantum Red |
| PE-Cy7 conjugates | 480; 565; 743 | 767 | | |
| APC-Cy7 conjugates | 650; 755 | 767 | | PharRed |
| Red 613 | 480; 565 | 613 | | PE-Texas Red |
| Fluorescein | 495 | 519 | 389 | FITC; pH sensitive |
| FluorX | 494 | 520 | 587 | (AP Biotech) |
| BODIPY-FL | 503 | 512 | | |
| Tetramethylrhodamine | 550 | 560-608 | 444 | TRITC |
| Tetramethylrhodamine isothiocyanate | 547 | 530-560 | | |
| X-Rhodamine | 570 | 576 | 548 | XRITC |
| Lissamine Rhodamine B | 570 | 590 | | |
| PerCP | 490 | 675 | | Peridinin chlorphyll protein |
| Texas Red | 589 | (603) 615 | 625 | Sulfonyl chloride |
| Allophycocyanin (APC) | 650 | 660 | 104 | |
| TruRed | 490, 675 | 695 | | PerCP-Cy5.5 conjugate |
| Alexa Fluor dyes (Molecular Probes) | | | | |
| Alexa Fluor 350 | 346 | 445 | 410 | |
| Alexa Fluor 430 | 430 | 545 | 701 | |
| Alexa Fluor 488 | 494 | 517 | 643 | |
| Alexa Fluor 532 | 530 | 555 | 724 | |
| Alexa Fluor 546 | 556 | 573 | 1079 | |
| Alexa Fluor 555 | 556 | 573 | 1250 | |
| Alexa Fluor 568 | 578 | 603 | 792 | |
| Alexa Fluor 594 | 590 | 617 | 820 | |
| Alexa Fluor 633 | 621 | 639 | 1200 | |
| Alexa Fluor 647 | 650 | 668 | 1250 | |
| Alexa Fluor 660 | 663 | 690 | 1100 | |
| Alexa Fluor 680 | 679 | 702 | 1150 | |
| Alexa Fluor 700 | 696 | 719 | | |
| Alexa Fluor 750 | 752 | 779 | | |
| Spectrum dyes (Vysis) | | | | |
| SpectrumOrange | 559 | 588 | | |
| SpectrumGreen1 | 497 | 524 | | |
| SpectrumGreen$^2$ | 509 | 538 | | |
| SpectrumAqua | 433 | 480 | | |
| SpectrumBlue | 400 | 450 | | |
| SpectrumGold | 530 | 555 | | |
| SpectrumRed | 592 | 612 | | |
| SpectrumFRed (far red) | 655 | 675 | | |
| Cy Dyes (AP Biotech) | | | | |
| Cy2 | 489 | 506 | 714 | |
| Cy3 | (512); 550 | 570; (615) | 767 | |
| Cy3.5 | 581 | 596; (640) | 1102 | |
| Cy5 | (625); 650 | 670 | 792 | |
| Cy5.5 | 675 | 694 | 1128 | |
| Cy7 | 743 | 767 | 818 | |

Unlabelled binding members may be used as known in the art, by use of a second labelling step with e.g. a secondary antibody against the unlabelled binding members, said antibody being labelled as discussed above, such as fluorochrome labelled. By this two-step it may be possible to enhance the signals from the foetal cells. Further detection steps may be included by using indirect labelling as described here below.

Labelling

In one embodiment of the invention a binding member (such as an antibody) or a synthetic probe is directly labelled, by having fluorochromes covalently attached thereto. The binding of such probes or binding member to the target in the cell may be observed under a microscope as a bright fluorescence or may be detected by a fluorimetric apparatus.

Instead of direct labelling or in addition to the direct labelling in another embodiment the probes or binding members are indirectly labelled with biotin or enzymes for example, such as alkaline phosphatase or peroxidase. Biotin may be detected using suitable streptavidin/avidin molecules know to people skilled in the art. These complexes may comprise fluorochromes or suitable enzymes.

By use of a combination of labelling methods it is possible to enhance the signals from the foetal cells, thereby facilitating the identification thereof.

In order to enhance the probability and/or selectivity of identifying the foetal cells over the background of maternal cells, two or more selective labellings may be performed. The two or more labellings may be a combination of any of the labellings used for single labelling described above. Accordingly, the combined labelling may be carried out by the use of two or more different hybridisation probes, such as a combination of a DNA probe and a PNA probe for hybridisation with the same foetal RNA or more preferred with different foetal RNAs. Also, two or more different DNA probes (or PNA probes, or similar probes capable of specific hybridisation) may be used for hybridisation with different foetal RNAs. Likewise a combination of different binding members may be used, either with specificity for the same foetal antigen or with specificity for different antigens. In further embodiments labelling with a combination of nucleotide probes and binding members may be performed.

Use of a Binding Member According to the Invention

The identification of a new foetal cell using the method according to the invention have opened the possibility to use binding members, such as binding members identified as described herein for various application. Such binding members may be useful in several assay method such as for the purpose of pre-natal diagnosis or for the purpose of isolating a population of foetal cells. Such binding members may be used as described above for selectively label ling of foetal cells which may be processed further depending on the purpose of the assay.

In a further aspect the invention relates to an assay method comprising the steps of;
  a. providing a maternal blood sample and
  b. selectively labelling at least one foetal cell by labelling of a foetal cell antigen according to the invention or
  a. providing a maternal blood sample and
  b. selectively labelling at least one foetal cell by use of a binding member according to the invention,
    in said blood sample.

An embodiment of the invention relates to an assay method for identifying at least on foetal cell by use of a binding member as described herein, recognising a foetal cell type specific protein of morphological characteristics as described herein. Said at least on foetal cell may for example be selectively labelled using an immunodetection technique by use of a binding member, particular a binding member specifically recognizing the foetal cell identified by the method of the invention.

The invention further relates to an assay as described here above, comprising one or more steps of labelling foetal cell as described herein for specific purposes. The assay method may include steps of labelling foetal cell antigens of mRNA of foetal cell antigens such as the previously known foetal cell antigens described in the section related thereto.

Isolation of Foetal Cells

Selective labelling of foetal cells using the binding member according to the invention may in a further embodiment be used for selection of foetal cells recognized by the binding member. By use of suitable techniques known in the art, the selectively labelled cells may be isolated from the cell sample and processed further. The isolated foetal cells may be used for pre-natal diagnosis or for specific application related to the cell type isolated (see below)

In further embodiment the assay may be for determination of gender or chromosomal abnormalities.

Pre-Natal Gender Determination

The findings according to the present invention may further be used for determination of gender of the foetus, either by use of male specific probes or by employing antigen binding members identified by the method described herein for the detection of foetal cells, followed by suitable methods for determination of gender known to a person skilled in the art.

Prenatal Diagnosis of Chromosomal Abnormality

In parallel to determination of gender, the invention further relates to methods for determination of chromosomal abnormalities by detection of foetal cells based on antigens or binding member recognising said foetal cell antigens isolated or identified based on the present invention. Such methods of determination of chromosomal abnormalities relates to the detection of such as aneuploidy, translocation, unbalanced translocation, rearrangement, subtelomeric rearrangement, unbalance chromosomal rearrangement, unbalance subtelomeric rearrangement, deletion, inversions, unbalanced inversions, duplication and telomere instability and or shortening. The chromosomal abnormality may further be such as single nucleotide substitution, micro deletion, micro-insertion, short deletions, short insertion, multi-nucleotide changes, DNA methylation and/or loss of imprint. (LOI)

In a preferred embodiment chromosomal aneuploidy is a complete and/or partial trisomy. Such as trisomy 21, trisomy 18, trisomy 13, trisomy 16 and/or XXX and other sex chromosome abnormalties. Alternatively the aneuploidy is a complete and/or partial monosomy, such as monosomy X, monosomy 21, monosomy 22, monosomy 16 and/or monosomy 15.

DNA hybridisation techniques may be used for determination of gender or determination of chromosomal abnormalities. Techniques known in the art includes methods such as fluorescent in situ hybridization (FISH), primed in situ labelling (PRINS), quantitative FISH (Q-FISH) and multicolor-banding (MCB). Fluorescence in situ hybridization (FISH) makes use of molecular probes labelled as described above with e.g. a fluorescence. A probe corresponding to a gene or DNA sequence is used and shows a signal under a microscope at a specific locus on a chromosome. The FISH technique may be applied to interphase cells and may confirm the presence of an euploid or an aneuploid of chromosomes X, Y, 13, 15, 18, 21. FISH is useful for identifying abnormal numbers of chromosomes such as trisomies and monosomies and may, when probes are available for specific regions of chromosomes, be used to determine if deletions, translocations, or duplications are present.

As an alternative to the above mentioned hybridisation techniques PCR methods may be used for determining chromosomal abnormalities. PCR methods according to the invention includes suitable method known in the art, capable of detecting abnormalities as trisomies etc. as described above. PCR methods may further be employed for determination of minor abnormalities, such as small deletions of mutation in specific genes. Quantitative fluorescent PCR (QF-PCR) is an example of such methods suitable for detection of for example trisomy 13, 18, 21, triploidies, double trisomies as well as X and Y aneuploidies (V. Cirigliano, 2004). By the design of suitable primers for minor but none the less severe chromosomal abnormalities. PCR methods may be used for determination of disease such as for example Cystic Fibrosis which is often caused by a 3 bp deletion in the Cystic Fibrosis Gene leading to a protein which lacks a critical phenylalanine amino acid.

Foetal Stem Cell

The foetal cells as described above may be stem cells. Stem cells come in different varieties, relating to when and where they are produced during development, and how versatile they are. The foetal stem cells detected may be of any type, such as embryonic, or somatic, being pluripotent or multipotent.

Use of Stem Cells.

By applying the technology described herein, foetal stem cells may be isolated from a maternal blood samples by use of a binding member, antibody or antibody fragment recognising said foetal cell antigen according to the invention. Stem cells can produce more stem cells and they can be used to generate specialized cell types such as nerve, blood or liver cells. Depending on the types of stem cells isolated the cells may have varying application in the development of cells of specific cell types or tissue. Pluripotent stem cells may give rise to any cell type whereas multipotent stem cells may give rise to a more limited number of cell types. For example, blood-forming (haematopoietic) stem cells may be capable of forming all types of blood cells, whereas mesenchymal stem cells are capable of forming mesenchymal cells.

Stem cells, especially pluripotent stem cells may be used for treatment of a variety of disease. Pluripotent stem cells are traditionally embryonic stem cells, which due to ethical considerations are of limited availability. The possibility of using stem cells isolated from a maternal blood sample is an attractive alternative. Pluripotent stem cells may be used for treatment of a plurality of diseases for which conventional methods does not provide suitable treatment.

DETAILED DESCRIPTION OF THE DRAWINGS

FIG. 1
Detection of One Male Foetal Cell.

A slide comprising maternal blood cells prepared as in example 1, is hybridized with DXZ1 and DYZ1 probes labelled with spectrum green and spectrum orange as described in example 2. FIG. 1B shows the area of the male foetal cell after the first hybridisation wherein the spectrum orange label is indicated with an arrow. Following stripping and re-hybridisation with reversed labelling the labelling has switched confirming the male identity of the cell. The green labelling of the cell is indicated by the arrow on FIG. 1C. FIG. 1A shows an enlarged area of the slide after the second labelling again the male cell is indicated by an arrow.

FIG. 2
Shielding of Target Antigenic Material (Cells) from UV Light.

The figure shows a graphical view of a slide covered with cells, including a cell, for antibody selection. The slides are hybridized with phages and following "the cell" is covered with a puck protecting the cell, and the associated phages from damage during UV irradiation.

FIG. 3
Shielding of Target Antigenic Material (Cells) from UV Light Using a Shadow Stick.

The figure shows a situation as in FIG. 2, wherein the shielding is performed by a shadow stick.

FIG. 4
Reflection of UV Light.

The figure shows a drawing illustrating the problem of reflection of UV light. Non-vertical UV light may indirectly reach "the cell" and thus reduce the number of viable phages that can be eluted from the cell.

FIG. 5
Shielding of Target Antigenic Material (Cells) from Reflected UV Light Using a Cylinder.

A cylinder is placed around "the cell" to minimised the amount of reflected UV light.

FIG. 6
Graphic Illustration of ELISA Assay Results

Elisa data, obtained as described in example 8, is shown graphically. A The binding activity to K562 cells are measured in three different dilutions for each clone. B and C. The binding activity to lymphocytes and a blank ELISA plate is measured similarity for each clone.

Figure 7:
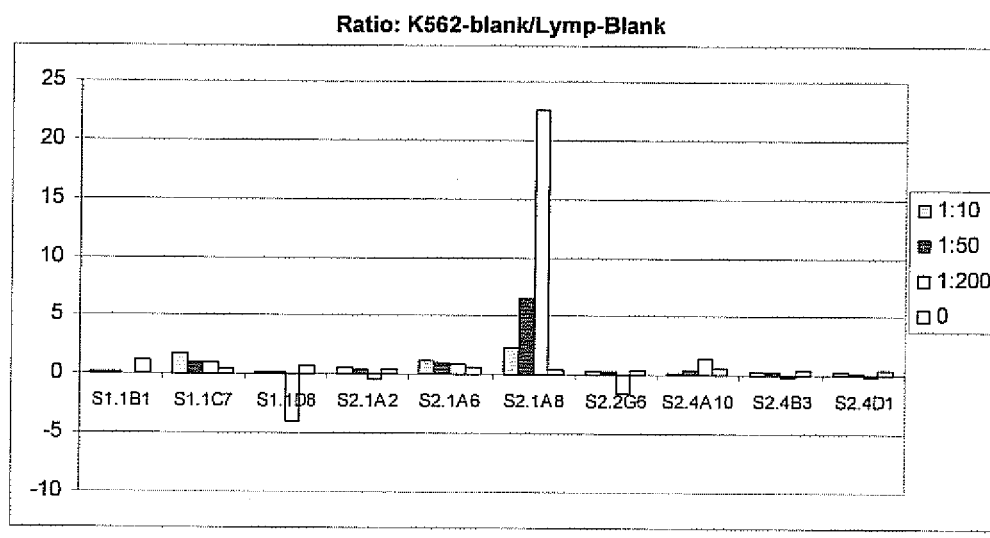
FIGS. 7A and 7B show the binding to K562 cells relative to the binding to lymphocytes. The same data as shown in FIG. 6 were evaluated by first taking the result for recognition of K562 shown in FIG. 6A and subtracting these values by the background in FIG. 6C, these values were then divided by the recognition of normal lymphocytes (FIG. 6B) minus the background (FIG. 6C). These values are presented in FIG. 7A and indicated how much better the individual antibodies bind to K562 compared to lymphocytes (fold change). 3 different dilutions of antibody were tested for each of the recombinant antibodies (1:10, 1:50 and 1:200).
Figure 7:
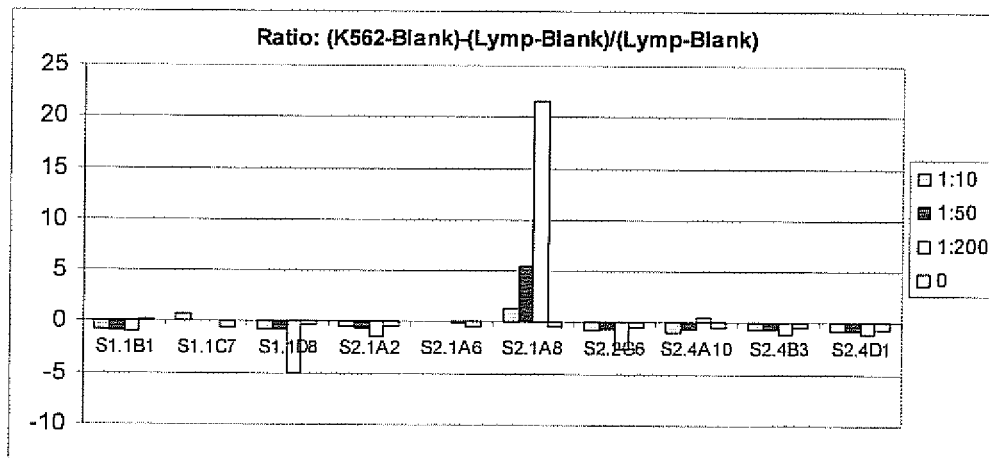

FIG. 7
Specificity of K562 binding.

The data shown in FIG. 6 is used to evaluate the specificity of the clones.

The rate of specificity is measured by the following equations:

$$R1 = K562\text{-blan/lymph-blank}$$

$$R2 = (K562\text{-Blank}) - (\text{Lympho-Blank})/\text{Lympho-Blank}$$

R1 is shown in FIG. 7A and R2 in FIG. 7B

EXAMPLES

Example 1

Preparation of Peripheral Blood from Pregnant Women

The maternal blood sample (usually 3 ml) is divided into aliquots of 1 ml. Each aliquot is diluted 1:14 with 0.15 M NaCl, and the cells are allowed to sediment over night at 4° C. After sedimentation, the upper 12 ml of the supernatants are carefully removed and pooled.

The sedimented cells (total volume 2 ml/tube) are divided into aliquots of 0.5 ml.

Pre-Fixation without Erythrocyte Lysis

Cells of the supernatant is pre-fixed in a paraformaldehyde solution in PBS, with a final concentration of 0.5% of PFA for 10 minutes.

Recovering and Mounting on Slides

The cells are recovered by centrifugation for 10 minutes at 500 g. After centrifugation, the supernatant is discarded and the cell pellet is re-suspended in 0.15 M NaCl (usually 20 µl) and smeared onto poly-L-lysine coated slides (usually 2 slides).

Pre-Fixation with NH$_4$Cl Mediated Erythrocyte Lysis

Each aliquot of the sedimented cells is diluted with 10 ml of 29° C. hot reagent mixture consisting of 1 part $10^{-3}$ M acetazolamide, 9 parts 0.15 M NaCl, and 90 parts 0.1844 M NH$_4$Cl. After incubation for 2 minutes at 29° C., 200 µl 30 mM NH$_4$HCO$_3$ is added and the cell suspension is incubated at 29° C. until erythrocytes are lysed (usually 10-15 minutes).

The cells are then pre-fixed for 10 minutes by adding PFA to an end concentration of 0.43%, that is 1.3 ml 4% PFA in PBS if the sample are process directly from erythrocyte lysis.

Recovering and Mounting on Slides

The cells are recovered by centrifugation for 10 minutes at 500 g.

The cell pellet is resuspended in 0.15 M NaCl (usually 100 µl isotonic salt solution per ml whole blood) and smeared onto poly-L-lysine coated slides (usually 10 µl cell suspension per slide). After air-drying over night, the slides are sealed individually in airtight plastic backs and stored at −20° C. until hybridization.

Example 2

Identification of Male Fetal Cells by Reverse Color Fish and Automated Scanning

Slides are recovered from the freezer and the airtight plastic back is removed. Before hybridization, slides are fixed and permeabilised 10 minutes in −20° C. cold methanol, 10 minute in −20° C. cold acetone and rinsed in phosphate buffered saline (PBS). Slides are then fixed again for 10 minutes in 2% PBS buffered paraformaldehyde (PFA) and rinsed for 5 minutes in PBS before they are dehydrated 3 minutes each in 60%, 80% and 99.9% ethanol and air-dried.

Chromosome-specific repeat probes, DXZ1 labeled with spectrum green and DYZ1 Labeled with spectrum orange (Vysis) are used for the first hybridization. Hybridization mixture containing both probes is prepared by mixing 1 part of the X-probe, 1 part of the Y-probe, 1 part of distilled water, and 7 parts of hybridization buffer (Vysis). For whole slide FISH, 28 µl of the hybridization mixture is added and covered by a 22×50 mm cover slips. Cover slips are sealed with rubber cement and the DNA's are denatured on a hot plate at 83.5° C. for 7 minutes and hybridized overnight in a humidified atmosphere at 42 C.

The next day hybridized slides are washed for 2 minutes in 0.4×SSC/0.3% Tween 20 at 73° C. and for 1 minute in 2×SSC/0.1% Tween 20 at room temperature. The slides are then mounted in Vectashield with 0.6 µg/ml DAPI as counter stain.

Cells containing a red signal located in a DAPI stained nucleus is identified by automatic scanning at 20× magnification of slides using scan function 5 in the MDS slide-scanning system developed by Applied Imaging. After scanning, cells identified by the scanner are inspected visually by automatic relocation using the multi-filter acquisition setup. Cells that have one red signal (a putative Y-signal) but two green X-signals are discarded, while cells that have one red signal and one green X-signal or a split green X-signal are classified as candidate fetal male cells.

The true fetal origin of the candidate fetal cells is analyzed by re-hybridization of candidate cells with the same probes in reverse colors. First, the cover slips are removed and the slides are washed in 4×SSC/0.1% Tween 20 for 10 minutes, rinsed in 2×SSC, dehydrated through 60%, 80%, and 99.9% ethanol and air-dried.

Hybridization mixture containing 1 part of the chromosome-specific repeat probes, DXZ1 labeled with spectrum red, 1 part of the chromosome-specific repeat probe DYZ1 labeled with spectrum green, 1 part distilled water, and 7 parts hybridization buffer (Vysis) is used for re-hybridization.

For whole slide FISH, 28 µl of the hybridization mixture is added and covered by a 22×50 mm cover slips. For selective FISH, 2.5 µl hybridization mixture is applied at positions on the slides where candidate fetal cells had been found and the mixture is spread by covering with a 10 mm circular cover slip. Cover slips are then sealed with rubber cement, and DNA's is denatured on a hot plate at 83.5° C. for 7 minutes and hybridized overnight in a humidified atmosphere at 42° C.

After re-hybridization slides are washed for 2 minutes in 0.4×SSC/0.3% Tween 20 at 73° C. and for 1 minute in 2×SSC/0.1% Tween 20 at room temperature. The slides are then mounted in Vectashield containing 0.6 µg/ml DAPI as counterstain.

Re-hybridized slides are placed in the scanning microscope and re-hybridized candidate fetal cells are relocated using the multifilter acquisition setup and FISH signals are analyzed visually. Re-hybridized candidate fetal cells where the red signal remains red and the green signal has switched to red are classified as false fetal cells, whereas re-hybridized candidate fetal cells where the red signal has switched to green and the green signal to red are classified as true fetal cells.

Y Chromosome Control Procedure

Blood samples are drawn before an invasive procedure. Only blood samples from women pregnant with a male fetus is analyzed for the presence of male (XY) fetal cells using reverse color FISH with sex chromosome specific X and Y probe mixtures. The gender of the fetus is established by interphase fluorescent in situ hybridization (FISH) on part of the CVS sample/amniocytes or by routine ultrasound scanning.

Probes

The X-Y specific probes are obtained from Vysis inc. The DYZ1 probe recognises Satellite III DNA on Yq12, while DXZ1 recognise Alpha Satellite DNA Xp11.1-q11.

Example 3

Generation of Foetal Cell Specific Antibody Fragments

Foetal cell specific antibody fragments against cell markers are generated by use of phage display.

Based on the identification of foetal cells by FISH, the localization of the foetal cell on the slides is known. The identified foetal cell is subjected to biopanning whereby single chain fragment variable (scFv) antibody fragments are generated.

The selection of antibody fragments may be preformed as follows.

1. The slide is blocked for 1 hour in 2% MPBS (skimmed milk powder in 1×PBS) at room temperature in order to reduce the amount of unspecific binding. This is done by subjecting the slide into MPBS in a holder for slides.

2. The slide is washed one time in 1×PBS

3. Biopanning: the scFv phage library (McCafferty et al. 1990) is incubated with the slide in 2% MPBS for one hour, with gentle shaking. A suitable library may have a semi-synthetic $V_H$+$V_L$ repertoire and two single framework repertoires. An input of $10^{12}$-$10^{13}$ phages is used, to cover the diversity of the repertoire.

4. The slide is washed 2 times with 1×PBS Tween (1×PBS added 0.05% Tween 20) followed by 3 washes with 1×PBS, for 3 minutes each with gently shaking.

5. Capture of the cell may be performed by either by Laser capture micro-dissection (LCM) (Lu et al., 2004) or by micro-dissection.

6. Bound phages are eluted from the retrieved cell. Trypsin is added to the cell, (100 µl, 1 mg/ml) for 10 min.

7. Eluted phages are incubated with E. coli. TG-1 (supE hsdD5 (lac-proAB)thi F'[traD36 pro AB+ lacl$^q$ lacZ]) for 45 min at 37° C., to allow infection of the cells through the F-pillus.

8. The infected culture is plated on TYE agar plates containing 1% glucose and 100 µg/ml ampicillin. The plate is incubated at 30° C. over night, allowing colonies to form.

9. All colonies are picked and grown monoclonal in 96 well microtitre plates. Each well containing cells producing one antibody fragment displayed on phage. Each will be grown in large scale for testing of specificity.

Example 4

Characterisation of Foetal Cell Specific Binding Members

Following isolation of binding members the specificity of the binding members for foetal cell specific is evaluated.

The testing of antibody fragment specificity may be performed by a series of steps as describe here below.

1. Binding members recognizing adult blood cells are excluded. This is performed by testing the phage displayed antibody fragments in Enzyme-linked immunosorbent assays (ELISA) against adult blood cells from a non-pregnant person. ELISA plates are coated by adding 10,000-100,000 blood cells per well and plates are allowed to dry. According to the invention this is the most suitable method of coating the ELISA plates with blood cells, although other methods may be applied. Phages binding these non-foetal blood cells are following excluded.

2. The remaining binding members are tested in ELISA against different cell cultures such as embryonic, foetal and stem cell cultures. If any cell lines are similar or related to the identified foetal cell, this may preferably be used for the ELISA.

3. The selected binding members are subcloned in suitable vectors, such as the pKBJ3 vector (Jensen et al., 2002) which are used for phages, for large scale expression of the binding members. These binding members such as scFv antibodies are used for staining of foetal blood samples to analyse the specificity and localization of the antigen. Once the specificity of the antibody is confirmed, the next step the identification of the cell marker/antigen is performed.

Example 5

Identification of Cell Marker/Antigen

Immunoprecipitation and/or 2D PAGE followed by Mass Spectroscopy for identification of foetal cell antigens recognized by the identified binding member.

Immunoprecipitation is preformed by biotinylating the antibodies and incubating these with streptavidin coated DYNA beads, followed by washing away the unbound antibodies. The beads are then incubated with foetal cells (or cell culture cells if these are recognised by the antibody). A detergent is added and the beads retrieved binding the antigen to the antibody. This sample is analysed by SDS-PAGE, the band(s) cut out and analysed mass spectroscopy whereby the antigen is identified. When the antibody is capable of recognising the antigen in denatured condition, a 2D gel analysis may be performed. Cells are run on the gel and the proteins transferred to a nitrocellulose membrane. A western blot is performed with the antibody, revealing a "spot" that is cut out and analysed by mass spectroscopy.

Example 6

Identification of Foetal Cells by the Presence of Cell Type Specific Proteins Antibody staining using isolated antibodies specifically recognizing foetal cells. Slides are fixed 10 minutes in −20° C. cold methanol, 10 minutes in −20° C. cold acetone and rinsed in PBS. They are then fixed 10 minutes in 2% PBS buffered paraformaldehyde, rinsed in PBS and dehydrated in increasing concentrations of ethanol. After air drying, slides are pre-incubated for 10 minutes at RT with 100 µl of blocking buffer consisting of 4×SSC containing 1% BSA and 0.5% blocking reagent (Boehringer Manheim). Slides are then incubated for 30 minutes at RT with 100 µl antibody solution diluted in blocking buffer according to manufactures instructions. After antibody incubation, slides are washed three times for 5 minutes in 4×SSC. To detect antibody bound to foetal cells, the slides are incubated with 100 µl biotinylated goat anti-mouse antibody (Delco, Glostrup, Denmark, diluted 1:25 in blocking buffer) for 30 minutes at RT, washed two times for 5 minutes in 4×SSC, and incubated with 100 µl of streptavidin conjugated to FITC or Cy3 (DAKO, Glostrup, Denmark, diluted 1:100 in blocking buffer) for 30 minutes at RT. After washing two times for 5 minutes each in 4×SSC and one time for 5 minutes in 2×SSC, slides were air dried and mounted with antifade Vectashield containing 4,6-diamidino-2-phenylindole (DAPI) to counterstain the nuclei.

Example 7

Chromosome Analysis of Foetal Cells from Maternal Blood

Analysis of numerical chromosome 13, 18, 21, X and Y abnormalities in foetal cells from maternal blood is done by FISH using the AneuVision DNA Probe Kit from Vysis Inc. Before hybridization, the slides are fixed 10 minutes in −20° C. cold methanol, 10 minutes in −20° C. cold acetone and rinsed in PBS. They are then fixed 10 minutes in 2% PBS buffered paraformaldehyde, rinsed in PBS and dehydrated in increasing concentrations of ethanol and air-dried. 10 µl of the probe mixture is added and covered by a 22×22 mm coverslip. The coverslip is sealed with rubber cement and the DNA's are denatured on a hot plate for 1 minute at 75° C. and hybridized over night in a humidified atmosphere at 37-42° C. The next day hybridized slides are washed at 72° C. for 2 minutes in 0.4×SSC/0.3% Tween 20 followed by 1 minute in 2×SSC/0.1% Tween at room temperature. The slides are mounted in Vectashield with 0.6 µg/ml DAPI as counterstain.

Example 8

Use of Phage-Library for Generation of Antibody Fragments Specific for H562 Cells Slide with double hybridized male blood with a spike of K562 cells on top is used as.

Incubation Procedure

Slides are submerged in PBS and the coverslide is removed.

Slides are blocked for 1-2 hours in 2% MPBS (2% Marvel skimmed milk powder in PBS)

Wash slides two times with PBS

Incubate with phage library for 1 hour; approximately $10^{13}$ phage added in 2% MPBS.

Slides are washed 3 times with PBS and stored in a 10% glycerol solution to avoid drying out of the slide.

UV Irradiation

Slide is placed in slideholder on microscope, and an area of cells comprising target antigenic material is selected and complete drying of the slide during the procedure is avoided.

Shadow-stick, puck, or other UV shielding protection is placed over selected area.

Slide is irradiated with UV-C (254 nm) light for 5 min; distance approximately 2 cm.

The protected area is marked, so that the location is known for the elution of phages.

Phage Elution

50 µl of 1 mg/ml trypsin in buffer (100 mM Tris-HCl, 1 mM CaCl$_2$) is added to the area on the slide with the protected cell(s) for 10 min.

Alternatively the phages may be eluted at a low pH

Buffer for elution: 50 mM Glycine, pH 2,2; neutralize min 1 h with Tris-HCL.

The liquid is transferred to an eppendorf tube. Area washed with 200 µl of PBS that is added to the same tube Phage Infection 800 µl of TG-1 culture in log-phase is added to half the eluted phage (the other half is retained for infection the following day). Incubated at 37° C. for 30-45 min.

Cells are spun down, 800 µl of the supernatant is removed. The remaining is resuspended and plated on TYE plates containing ampicillin.

Plates are incubated at 30° C. over night and analysed next day.

Selection of Antigen Specific Phages

Phages from the selected area of the slides are eluted according to the scheme here below.

| Slide number | Elution | First Half | Second Half | Total |
|---|---|---|---|---|
| 1 | Trypsine | 4 | 4 | 8 |
| 2 | Trypsine | 3 | 1 | 4 |
| 3 | Trypsine | 5 | 17 | 22 |
| 4 | Acid | 1 | 2 | 3 |
| 5 | Acid | 0 | 3 | 3 |
| 6 | Acid | 0 | 1 | 1 |
| 7 | Trypsine | 12 | 353 | 365 |
| 8 | Trypsine | 1 | 2 | 3 |
| 9 | Acid | 0 | 0 | 0 |
| 10 | Acid | 0 | 10 | 10 |
| -stick | Trypsine | 0 | 7 | 7 |
| Total Amount | | 26 | 400 | 426 |

Following 384 antibody fragments (4 plates) are tested monoclonally in ELISA against K562 (fixed) and cells from lymphoprep (fixed) are selected.

The procedure is repeated several times and phage derived antibody fragments are test in ELISA. Below are the results from a series of selections. ELISA results are shown in the tables here below and graphically in FIGS. 6 and 7.

Series 1

K562

| | S1.1B1 | S1.1C7 | S1.1D8 | S2.1A2 | S2.1A6 | S2.1A8 | S2.2G6 | S2.4A10 | S2.4B3 | S2.4D1 |
|---|---|---|---|---|---|---|---|---|---|---|
| 1:10 | 0.06 | 1.041 | 0.057 | 0.125 | 0.336 | 1.97 | 0.074 | 0.051 | 0.215 | 0.145 |
| 1:10 | 0.061 | 0.778 | 0.068 | 0.146 | 0.369 | 2.007 | 0.083 | 0.063 | 0.243 | 0.187 |
| 1:50 | 0.036 | 0.175 | 0.047 | 0.06 | 0.081 | 1.459 | 0.054 | 0.056 | 0.108 | 0.075 |
| 1:50 | 0.037 | 0.144 | 0.044 | 0.055 | 0.089 | 1.443 | 0.052 | 0.049 | 0.102 | 0.075 |
| 1:200 | 0.032 | 0.061 | 0.036 | 0.053 | 0.05 | 0.838 | 0.044 | 0.039 | 0.049 | 0.043 |
| 1:200 | 0.035 | 0.074 | 0.043 | 0.047 | 0.061 | 0.85 | 0.048 | 0.049 | 0.061 | 0.058 |
| 0 | 0.04 | 0.05 | 0.048 | 0.054 | 0.055 | 0.058 | 0.058 | 0.06 | 0.063 | 0.062 |
| 0 | 0.038 | 0.046 | 0.047 | 0.051 | 0.05 | 0.054 | 0.053 | 0.057 | 0.057 | 0.054 |

Lympho

| | S1.1B1 | S1.1C7 | S1.1D8 | S2.1A2 | S2.1A6 | S2.1A8 | S2.2G6 | S2.4A10 | S2.4B3 | S2.4D1 |
|---|---|---|---|---|---|---|---|---|---|---|
| 1:10 | 0.131 | 0.484 | 0.119 | 0.191 | 0.314 | 0.857 | 0.135 | 0.102 | 0.493 | 0.476 |
| 1:10 | 0.149 | 0.58 | 0.135 | 0.203 | 0.318 | 0.92 | 0.161 | 0.1 | 0.51 | 0.526 |
| 1:50 | 0.067 | 0.149 | 0.064 | 0.084 | 0.082 | 0.254 | 0.064 | 0.062 | 0.203 | 0.212 |
| 1:50 | 0.06 | 0.158 | 0.063 | 0.07 | 0.088 | 0.274 | 0.069 | 0.061 | 0.215 | 0.182 |
| 1:200 | 0.04 | 0.064 | 0.039 | 0.048 | 0.052 | 0.08 | 0.05 | 0.043 | 0.069 | 0.094 |
| 1:200 | 0.041 | 0.068 | 0.05 | 0.056 | 0.061 | 0.096 | 0.062 | 0.053 | 0.093 | 0.098 |
| 0 | 0.038 | 0.055 | 0.049 | 0.059 | 0.059 | 0.062 | 0.067 | 0.065 | 0.074 | 0.069 |
| 0 | 0.038 | 0.053 | 0.05 | 0.059 | 0.058 | 0.062 | 0.062 | 0.066 | 0.067 | 0.067 |

Blank

| | S1.1B1 | S1.1C7 | S1.1D8 | S2.1A2 | S2.1A6 | S2.1A8 | S2.2G6 | S2.4A10 | S2.4B3 | S2.4D1 |
|---|---|---|---|---|---|---|---|---|---|---|
| 1:10 | 0.03 | 0.062 | 0.039 | 0.048 | 0.056 | 0.078 | 0.048 | 0.041 | 0.055 | 0.046 |
| 1:10 | 0.032 | 0.056 | 0.041 | 0.052 | 0.06 | 0.079 | 0.047 | 0.047 | 0.055 | 0.047 |
| 1:50 | 0.035 | 0.049 | 0.046 | 0.051 | 0.051 | 0.055 | 0.057 | 0.055 | 0.057 | 0.054 |
| 1:50 | 0.034 | 0.045 | 0.041 | 0.046 | 0.047 | 0.053 | 0.049 | 0.049 | 0.051 | 0.048 |
| 1:200 | 0.031 | 0.039 | 0.038 | 0.039 | 0.04 | 0.039 | 0.042 | 0.041 | 0.045 | 0.041 |
| 1:200 | 0.034 | 0.047 | 0.044 | 0.049 | 0.047 | 0.051 | 0.05 | 0.053 | 0.055 | 0.051 |
| 0 | 0.033 | 0.047 | 0.043 | 0.052 | 0.05 | 0.055 | 0.054 | 0.058 | 0.06 | 0.058 |
| 0 | 0.034 | 0.043 | 0.042 | 0.045 | 0.042 | 0.049 | 0.046 | 0.05 | 0.049 | 0.05 |

K562

|       | S1.1B1 | S1.1C7 | S1.1D8 | S2.1A2 | S2.1A6 | S2.1A8 | S2.2G6 | S2.4A10 | S2.4B3 | S2.4D1 |
|-------|--------|--------|--------|--------|--------|--------|--------|---------|--------|--------|
| 1:10  | 0.0605 | 0.9095 | 0.0625 | 0.1355 | 0.3525 | 1.9885 | 0.0785 | 0.057   | 0.229  | 0.166  |
| 1:50  | 0.0365 | 0.1595 | 0.0455 | 0.0575 | 0.085  | 1.451  | 0.053  | 0.0525  | 0.105  | 0.075  |
| 1:200 | 0.0335 | 0.0675 | 0.0395 | 0.05   | 0.0555 | 0.844  | 0.046  | 0.044   | 0.055  | 0.051  |
| 0     | 0.039  | 0.048  | 0.0475 | 0.0525 | 0.0525 | 0.056  | 0.0555 | 0.0585  | 0.06   | 0.058  |

Lympho

|       | S1.1B1 | S1.1C7 | S1.1D8 | S2.1A2 | S2.1A6 | S2.1A8 | S2.2G6 | S2.4A10 | S2.4B3 | S2.4D1 |
|-------|--------|--------|--------|--------|--------|--------|--------|---------|--------|--------|
| 1:10  | 0.14   | 0.532  | 0.127  | 0.197  | 0.316  | 0.8885 | 0.148  | 0.101   | 0.5015 | 0.501  |
| 1:50  | 0.0635 | 0.1535 | 0.0635 | 0.077  | 0.085  | 0.264  | 0.0665 | 0.0615  | 0.209  | 0.197  |
| 1:200 | 0.0405 | 0.066  | 0.0445 | 0.052  | 0.0565 | 0.088  | 0.056  | 0.048   | 0.081  | 0.096  |
| 0     | 0.038  | 0.054  | 0.0495 | 0.059  | 0.0585 | 0.062  | 0.0645 | 0.0655  | 0.0705 | 0.068  |

Blank

|       | S1.1B1 | S1.1C7 | S1.1D8 | S2.1A2 | S2.1A6 | S2.1A8 | S2.2G6 | S2.4A10 | S2.4B3 | S2.4D1 |
|-------|--------|--------|--------|--------|--------|--------|--------|---------|--------|--------|
| 1:10  | 0.0335 | 0.0525 | 0.0435 | 0.0515 | 0.0555 | 0.067  | 0.052  | 0.051   | 0.056  | 0.051  |
| 1:50  | 0.0325 | 0.042  | 0.0395 | 0.0425 | 0.0435 | 0.046  | 0.0455 | 0.045   | 0.048  | 0.045  |
| 1:200 | 0.0335 | 0.047  | 0.0435 | 0.0505 | 0.0485 | 0.053  | 0.052  | 0.0555  | 0.0575 | 0.055  |
| 0     | 0.034  | 0.043  | 0.042  | 0.045  | 0.042  | 0.049  | 0.046  | 0.05    | 0.049  | 0.05   |

K562-Blank/Lympho-Blank

|       | S1.1B1 | S1.1C7 | S1.1D8 | S2.1A2 | S2.1A6 | S2.1A8 | S2.2G6 | S2.4A10 | S2.4B3 | S2.4D1 |
|-------|--------|--------|--------|--------|--------|--------|--------|---------|--------|--------|
| 1:10  | 0.2535 | 1.7873 | 0.2275 | 0.5773 | 1.1401 | 2.339  | 0.276  | 0.12    | 0.3883 | 0.256  |
| 1:50  | 0.129  | 1.0538 | 0.25   | 0.4348 | 1      | 6.445  | 0.3571 | 0.45455 | 0.354  | 0.2    |
| 1:200 | 0      | 1.0789 | −4     | −0.333 | 0.875  | 22.6   | −1.5   | 1.53333 | −0.106 | −0.096 |
| 0     | 1.25   | 0.4545 | 0.7333 | 0.5357 | 0.6364 | 0.5385 | 0.5135 | 0.54839 | 0.5116 | 0.444  |

(K562-Blank)-(Lympho-Blank)/Lympho-Blank

|       | S1.1B1 | S1.1C7 | S1.1D8 | S2.1A2 | S2.1A6 | S2.1A8 | S2.2G6 | S2.4A10 | S2.4B3 | S2.4D1 |
|-------|--------|--------|--------|--------|--------|--------|--------|---------|--------|--------|
| 1:10  | −0.746 | 0.7873 | −0.772 | −0.423 | 0.1401 | 1.339  | −0.724 | −0.88   | −0.612 | −0.744 |
| 1:50  | −0.871 | 0.0538 | −0.75  | −0.565 | 0      | 5.445  | −0.643 | −0.5455 | −0.646 | −0.8   |
| 1:200 | −1     | 0.0789 | −5     | −1.333 | −0.125 | 21.6   | −2.5   | 0.53333 | −1.106 | −1.096 |
| 0     | 0.25   | −0.545 | −0.267 | −0.464 | −0.364 | −0.462 | −0.486 | −0.4516 | −0.488 | −0.556 |

Series 2

Figure 8:
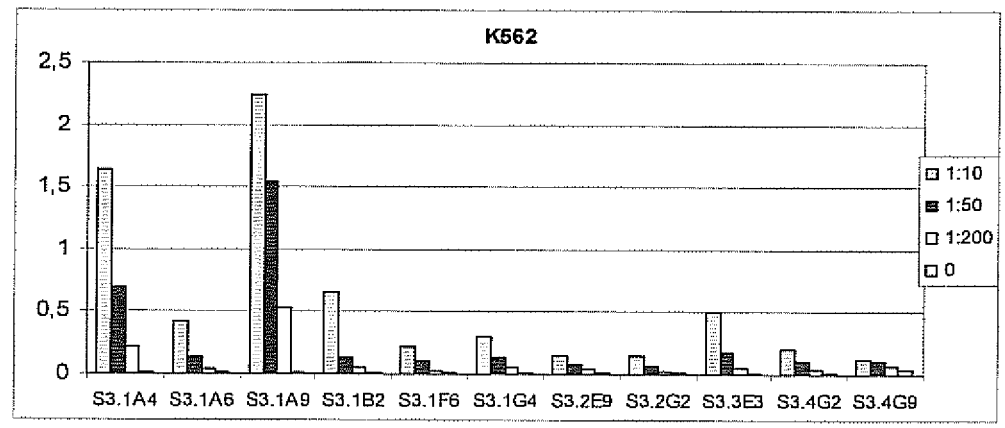
FIGS. 8A-8C show the same experiment as shown in FIG. 6, but with 11 new recombinant antibodies obtained by selection as specified in the example 8. The binding activity to K562 cells are measured in three different dilutions for each clone (FIG. 8A).
Figure 8:
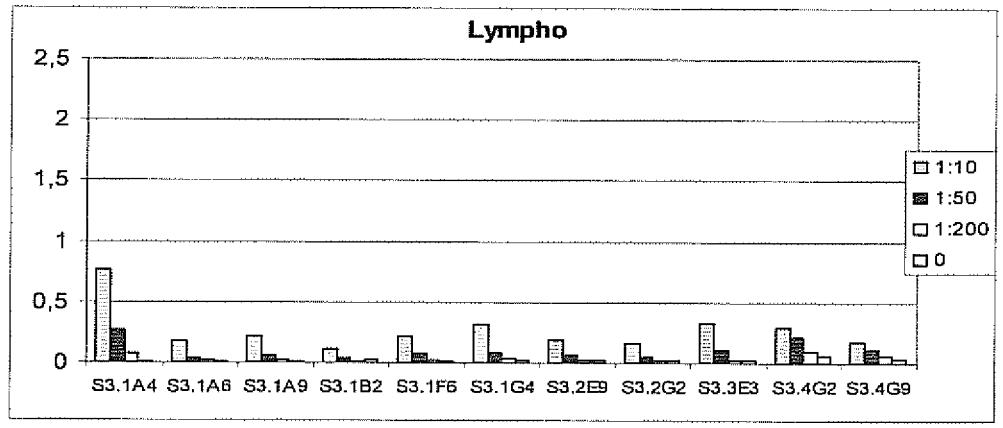
Figure 8:
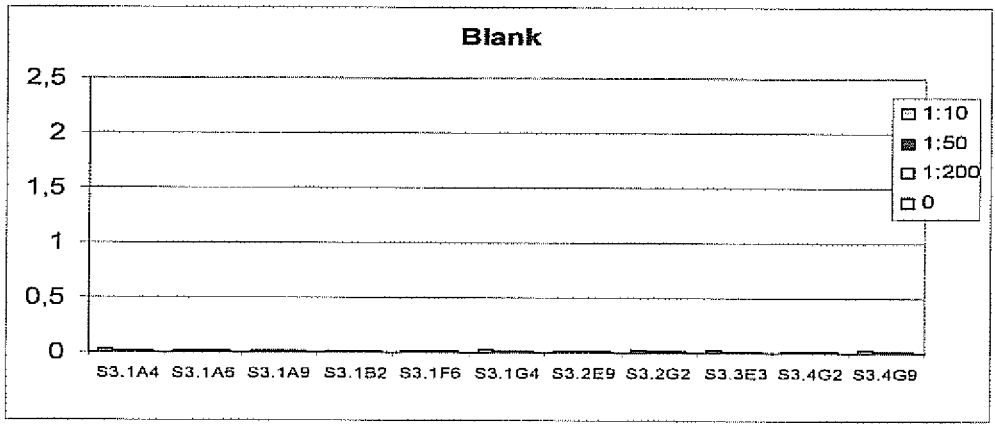

The data obtained in Series 2 is shown in the tables here below and in FIGS. 8 and 9.

K562

|       | S3.1A4 | S3.1A6 | S3.1A9 | S3.1B2 | S3.1F6 | S3.1G4 | S3.2E9 | S3.2G2 | S3.3E3 | S3.4G2 |
|-------|--------|--------|--------|--------|--------|--------|--------|--------|--------|--------|
| 1:10  | 1.555  | 0.403  | 2.127  | 0.628  | 0.186  | 0.249  | 0.122  | 0.124  | 0.474  | 0.167  |
| 1:10  | 1.73   | 0.436  | 2.352  | 0.689  | 0.257  | 0.346  | 0.184  | 0.165  | 0.532  | 0.248  |
| 1:50  | 0.73   | 0.134  | 1.551  | 0.072  | 0.114  | 0.138  | 0.081  | 0.058  | 0.185  | 0.118  |
| 1:50  | 0.673  | 0.13   | 1.548  | 0.201  | 0.102  | 0.133  | 0.085  | 0.073  | 0.158  | 0.09   |
| 1:200 | 0.211  | 0.044  | 0.545  | 0.054  | 0.027  | 0.054  | 0.037  | 0.02   | 0.055  | 0.042  |
| 1:200 | 0.215  | 0.039  | 0.512  | 0.061  | 0.036  | 0.056  | 0.042  | 0.022  | 0.055  | 0.045  |
| 0     | 0.01   | 0.019  | 0.013  | 0.022  | 0.019  | 0.02   | 0.021  | 0.022  | 0.022  | 0.023  |
| 0     | 0.011  | 0.01   | 0.01   | 0.012  | 0.01   | 0.02   | 0.017  | 0.018  | 0.015  | 0.016  |

Lympho

|       | S3.1A4 | S3.1A6 | S3.1A9 | S3.1B2 | S3.1F6 | S3.1G4 | S3.2E9 | S3.2G2 | S3.3E3 | S3.4G2 |
|---|---|---|---|---|---|---|---|---|---|---|
| 1:10  | 0.734 | 0.175 | 0.202 | 0.11  | 0.267 | 0.361 | 0.208 | 0.179 | 0.357 | 0.27  |
| 1:10  | 0.808 | 0.184 | 0.241 | 0.123 | 0.175 | 0.288 | 0.17  | 0.147 | 0.302 | 0.327 |
| 1:50  | 0.271 | 0.045 | 0.062 | 0.041 | 0.074 | 0.075 | 0.061 | 0.055 | 0.096 | 0.101 |
| 1:50  | 0.274 | 0.043 | 0.059 | 0.04  | 0.073 | 0.105 | 0.056 | 0.048 | 0.128 | 0.097 |
| 1:200 | 0.068 | 0.019 | 0.021 | 0.017 | 0.024 | 0.038 | 0.025 | 0.022 | 0.03  | 0.028 |
| 1:200 | 0.076 | 0.021 | 0.023 | 0.017 | 0.025 | 0.037 | 0.026 | 0.024 | 0.033 | 0.03  |
| 0     | 0.014 | 0.017 | 0.018 | 0.018 | 0.019 | 0.025 | 0.02  | 0.021 | 0.023 | 0.022 |
| 0     | 0.01  | 0.016 | 0.014 | 0.023 | 0.019 | 0.024 | 0.022 | 0.026 | 0.025 | 0.027 |

Blank

|       | S3.1A4 | S3.1A6 | S3.1A9 | S3.1B2 | S3.1F6 | S3.1G4 | S3.2E9 | S3.2G2 | S3.3E3 | S3.4G2 |
|---|---|---|---|---|---|---|---|---|---|---|
| 1:10  | 0.037 | 0.02  | 0.022 | 0.021 | 0.022 | 0.019 | 0.023 | 0.019 | 0.031 | 0.022 |
| 1:10  | 0.039 | 0.016 | 0.017 | 0.015 | 0.018 | 0.025 | 0.019 | 0.022 | 0.032 | 0.019 |
| 1:50  | 0.014 | 0.015 | 0.014 | 0.015 | 0.017 | 0.017 | 0.017 | 0.018 | 0.02  | 0.016 |
| 1:50  | 0.012 | 0.015 | 0.011 | 0.011 | 0.011 | 0.012 | 0.013 | 0.011 | 0.014 | 0.011 |
| 1:200 | 0.009 | 0.01  | 0.011 | 0.011 | 0.012 | 0.01  | 0.01  | 0.009 | 0.011 | 0.01  |
| 1:200 | 0.01  | 0.011 | 0.01  | 0.011 | 0.011 | 0.011 | 0.015 | 0.011 | 0.012 | 0.011 |
| 0     | 0.011 | 0.013 | 0.013 | 0.015 | 0.016 | 0.016 | 0.016 | 0.016 | 0.017 | 0.017 |
| 0     | 0.011 | 0.013 | 0.013 | 0.016 | 0.016 | 0.017 | 0.016 | 0.017 | 0.017 | 0.017 |

K562

|       | S3.1A4 | S3.1A6 | S3.1A9 | S3.1B2 | S3.1F6 | S3.1G4 | S3.2E9 | S3.2G2 | S3.3E3 | S3.4G2 |
|---|---|---|---|---|---|---|---|---|---|---|
| 1:10  | 1.6425 | 0.4195 | 2.2395 | 0.6585 | 0.2215 | 0.2975 | 0.153  | 0.1445 | 0.503  | 0.2075 |
| 1:50  | 0.7015 | 0.132  | 1.5495 | 0.1365 | 0.108  | 0.1355 | 0.083  | 0.0655 | 0.1715 | 0.104  |
| 1:200 | 0.213  | 0.0415 | 0.5285 | 0.0575 | 0.0315 | 0.055  | 0.0395 | 0.021  | 0.055  | 0.0435 |
| 0     | 0.0105 | 0.0145 | 0.0115 | 0.017  | 0.0145 | 0.02   | 0.019  | 0.02   | 0.0185 | 0.0195 |

Lympho

|       | S3.1A4 | S3.1A6 | S3.1A9 | S3.1B2 | S3.1F6 | S3.1G4 | S3.2E9 | S3.2G2 | S3.3E3 | S3.4G2 |
|---|---|---|---|---|---|---|---|---|---|---|
| 1:10  | 0.771  | 0.1795 | 0.2215 | 0.1165 | 0.221  | 0.3245 | 0.189  | 0.163  | 0.3295 | 0.2985 |
| 1:50  | 0.2725 | 0.044  | 0.0605 | 0.0405 | 0.0735 | 0.09   | 0.0585 | 0.0515 | 0.112  | 0.214  |
| 1:200 | 0.072  | 0.02   | 0.022  | 0.017  | 0.0245 | 0.0375 | 0.0255 | 0.023  | 0.0315 | 0.099  |
| 0     | 0.012  | 0.0165 | 0.016  | 0.0205 | 0.019  | 0.0245 | 0.021  | 0.0235 | 0.024  | 0.0625 |

Blank

|       | S3.1A4 | S3.1A6 | S3.1A9 | S3.1B2 | S3.1F6 | S3.1G4 | S3.2E9 | S3.2G2 | S3.3E3 | S3.4G2 |
|---|---|---|---|---|---|---|---|---|---|---|
| 1:10  | 0.0265 | 0.0155 | 0.0155 | 0.015  | 0.0175 | 0.021  | 0.018  | 0.02   | 0.026  | 0.0175 |
| 1:50  | 0.0105 | 0.0125 | 0.011  | 0.011  | 0.0115 | 0.011  | 0.0115 | 0.01   | 0.0125 | 0.0135 |
| 1:200 | 0.0105 | 0.012  | 0.0115 | 0.013  | 0.0135 | 0.0135 | 0.0155 | 0.0135 | 0.0145 | 0.0105 |
| 0     | 0.011  | 0.013  | 0.013  | 0.016  | 0.016  | 0.017  | 0.016  | 0.017  | 0.017  | 0.0105 |

K562-Blank/Lympho-Blank

|       | S3.1A4 | S3.1A6 | S3.1A9 | S3.1B2 | S3.1F6 | S3.1G4 | S3.2E9 | S3.2G2 | S3.3E3 | S3.4G2 |
|---|---|---|---|---|---|---|---|---|---|---|
| 1:10  | 2.1706 | 2.4634 | 10.796 | 6.3399 | 1.0025 | 0.911  | 0.7895 | 0.8706 | 1.5717 | 0.6762 |
| 1:50  | 2.6374 | 3.7937 | 31.081 | 4.2542 | 1.5565 | 1.5759 | 1.5213 | 1.3373 | 1.598  | 0.4514 |
| 1:200 | 3.2927 | 3.6875 | 49.238 | 11.125 | 1.6364 | 1.7292 | 2.4    | 0.7895 | 2.3824 | 0.3729 |
| 0     | −0.5   | 0.4286 | −0.5   | 0.2222 | −0.5   | 0.4    | 0.6    | 0.4615 | 0.2143 | 0.1731 |

(K562-Blank)-(Lympho-Blank)/Lympho-Blank

|       | S3.1A4 | S3.1A6 | S3.1A9 | S3.1B2 | S3.1F6 | S3.1G4 | S3.2E9 | S3.2G2 | S3.3E3 | S3.4G2 |
|-------|--------|--------|--------|--------|--------|--------|--------|--------|--------|--------|
| 1:10  | 1.1706 | 1.4634 | 9.7961 | 5.3399 | 0.0025 | −0.089 | −0.211 | −0.129 | 0.5717 | −0.324 |
| 1:50  | 1.6374 | 2.7937 | 30.081 | 3.2542 | 0.5565 | 0.5759 | 0.5213 | 0.3373 | 0.598  | −0.549 |
| 1:200 | 2.2927 | 2.6875 | 48.238 | 10.125 | 0.6364 | 0.7292 | 1.4    | −0.211 | 1.3824 | −0.627 |
| 0     | −1.5   | −0.571 | −1.5   | −0.778 | −1.5   | −0.6   | −0.4   | −0.538 | −0.786 | −0.827 |

Items
1. A method of detecting a foetal cell in a maternal blood sample comprising the following steps of:
   a. providing a maternal blood sample,
   b. fixing and permealizing nucleated cells present in said blood sample while;
      maintaining cell morphology,
      maintaining protein content of the cells and
      ensuring accessibility for a hybridisation probe,
   c. adding a hybridisation probe and
   d. detecting at least one foetal cell.
2. The method according to item 1, comprising a pre-fixation step.
3. The method according to item 2, wherein the pre-fixation step comprise PFA treatment.
4. The method according to item 3, wherein the pre-fixation step comprise incubation of cells in a solution comprising 0.1-4% PFA.
5. The method according to item 1, wherein the fixation and permeabilisation step comprises methanol and acetone treatment.
6. The method according to item 1, comprising a re-fixation step.
7. The method according to item 6, wherein the re-fixation step comprise PFA treatment.
8. The method according to item 7, wherein the re-fixation step comprise incubation of cells in a solution comprising 1-5% PFA.
9. The method according to item 1, comprising a dehydration steps in ethanol.
10. The method according to item 1, comprising an enrichment step.
11. The method according to item 10, wherein the enrichment step does not discriminate between different nucleated cell types.
12. The method according to item 11, wherein the enrichment step comprise a step of erythrocyte lysis.
13. The method according to item 12, wherein erythrocyte lysis is obtained in by $NH_4Cl$ mediated lysis.
14. The method according to item 1, wherein the foetal cell is detected by selective labelling of DNA in the foetal cell.
15. The method according to item 14, wherein cell type specific DNA is selectively labelled by a hybridisation technique.
16. The method according to item 1, wherein the foetal cell is detected by the presence of cell type specific epigenetic characteristics.
17. The method according to item 1, wherein the foetal cell is detected by selective labelling of cell type specific RNA in the foetal cell.
18. The method according to item 17, wherein cell type specific RNA is selective labelled by a hybridisation technique.
19. The method according to item 18, wherein the cell type specific RNA is an mRNA.
20. The method according to item 1, wherein the foetal cell is detected by selective labelling of at least one cell type specific protein.
21. The method according to item 1, wherein the foetal cell is detected by morphological characteristics.
22. The method according to any of the preceding items, wherein the detected foetal cell is a male foetal cell.
23. The method according to item 22, wherein the male foetal cell is detected by reverse colour FISH
24. The method according to any of the preceding items, wherein the at least one foetal cell is detected using an automated scanner system.
25. A foetal cell identified by the method according to item 1-24
26. A binding member specifically recognising the foetal cell according to item 25.
27. A foetal cell antigen recognised by the binding member according to item 26.
28. A method of isolating binding members recognizing target antigenic material of limited availability comprising the steps:
   a. identifying the target antigenic material,
   b. contacting said target antigenic material with a binding member generating system and
   c. isolating binding member(s) recognising the target antigenic material.
29. The method according to item 28 including a step of;
   d. minimizing the number binding members isolated recognizing non-target antigenic material.
30. The method according to item 28, wherein the binding member generating system allows linkage between the genotype and the phenotype of binding members generated by the system.
31. The method according to item 28, wherein the binding member generating system allowing linkage between the genotype and the phenotype of the binding member is selected from the group of; ribosome display, DNA display (including cis display), yeast display, bacterial display, retroviral display and phage display.
32. The method according to item 28, wherein the binding member generating system is phage display.
33. The method according to any of the items 28-32, wherein the ratio of target antigenic material $$R_{TA} = \frac{\text{target antigen material}}{\text{non-target antigen material}}$$

is less than 1/1000.
34. The method according to any of the items 28-33, wherein the target antigenic material may be limited to one cell.
35. The method according to any of the items 28-34, wherein the target antigenic material is a cell.
36. The method according to any of the items 28-35, wherein the target antigenic material is a cell in suspension.

37. The method according to any of the items 28-36, wherein the target antigenic material is a cell present on a slide.
38. The method according to any of the items 28-37, wherein the target antigenic material is a foetal cell.
39. The method according to any of the items 28-38, wherein the minimizing step comprises UV irradiation.
40. The method according to item 39, wherein the antigenic material and its associated binding members are protected from UV irradiation by shielding.
41. The method according to item 40, wherein shielding is obtained by use of an item selected from the group of; a puck, a shadow-stick.
42. The method according to item 41, wherein a cylinder is used for minimizing reflection of UV light.
43. The method according to item 28-42, wherein the binding member is selected from the group of antibodies, antibody fragments and non-immune binding members.
44. The method according to item 43, wherein the binding member is an antibody.
45. The method according to item 43, wherein the binding member is an antibody fragment.
46. The method according to item 43, wherein the binding member is a non-immune binding member.
47. A foetal cell antigen recognised by a binding member isolated using the method of item 28-46.
48. Binding members recognising a foetal cell antigen according to item 47.
49. An assay method comprising the steps of;
   a. providing a maternal blood sample,
   b. selectively labelling at least one foetal cell by labelling of a foetal cell antigen according to item 47 in said blood sample.
50. An assay method comprising the steps of:
   a. providing a maternal blood sample,
   b. selectively labelling at least one foetal cell by use of a binding member according to item 48 in said blood sample.
51. The assay according to any of the items 49-50, wherein said selectively labelled foetal cell is labelled by an immunodetection technique
52. The assay according to item 51, wherein the immunodetection technique comprise use of a binding member according to item 48.
53. The assay according to any of the items 49-52, comprising one or more of the characteristics of the method of detecting at least on foetal cell according to items 1-24.
54. The assay according to any of the items 49-53, wherein said selectively labelled foetal cell is isolated from the sample.
55. The assay according to item 54, wherein said selectively labelled foetal cell is isolated from the sample by FACS analysis.
56. The assay according to item 54, wherein said selectively labelled foetal cell is isolated from the sample by MACS analysis.
57. The assay according to item 54, wherein said selectively labelled foetal cell is subject to in situ chromosomal DNA analysis.
58. The assay according to any of the items 49-57 for determination of gender.
59. The assay according to any of the items 49-58 for determination of chromosomal abnormality.
60. The assay according to any of the items 58-59, wherein gender or chromosomal abnormality is determined by a DNA hybridisation technique.
61. The assay according to item 60, wherein the DNA hybridisation technique is selected from the group of; fluorescent in situ hybridization (FISH), primed in situ labeling (PRINS), quantitative FISH (Q-FISH) and multicolor-banding (MCB).
62. The assay according to item 61, wherein the DNA hybridisation technique is FISH.
63. The assay according to any of the items 57-59, wherein gender or chromosomal abnormality is determined by PCR.
64. The assay according to any of the items 49-63, wherein the maternal blood sample is from a pregnant woman at 6-15 weeks of gestation.

REFERENCES

Ager S, Nilson B H, Marling F J, Peng K W, Cosset F L, Russell S J. Retroviral display of antibody fragments; interdomain spacing strongly influences vector infectivity. Hum Gene Ther. 1996 Nov. 10; 7(17):2157-64.

Boder, E T, et al. Yeast surface display for screening combinatorial polypeptide libraries. Nat. Biotechnol. 1997 June; 15 (6):553-7.

Buchholz C J., Kah-Whye Peng, Frances J. Marling, Jie Zhang, Francois-Loic Cosset & Stephen J. Russell In vivo selection of protease cleavage sites from retrovirus display libraries pp 951-954, Nat. Biotechnol. 1998 October; 16(10):951-4.

Carter P, Kelley R F, Rodrigues M L, Snedecor B, Covarrubias M, Velligan M D, Wang W L, Rowland A M, Kotts C E, Carver M E, et al. High level *Escherichia coli* expression and production of a bivalent humanized antibody fragment. Biotechnology (N Y). 1992 February; 10(2):163-7.

V. Cirigliano, G. Voglino, M. P. Cañadas, A. Marongiu, M. Ejarque, E. Ordoñez, A. Plaja, M. Massobrio, T. Todros, C. Fuster, M. Campogrande, J. Egozcue and M. Adinolfi. Rapid prenatal diagnosis of common chromosome aneuploidies by QF-PCR. Assessment on 18 000 consecutive clinical samples. Molecular Human Reproduction, 2004: 10(11): 839-846.

Cumber A J, Ward E S, Winter G, Parnell G D, Wawrzynczak E J. Comparative stabilities in vitro and in vivo of a recombinant mouse antibody FvCys fragment and a bisFvCys conjugate. J Immunal. 1992 Jul. 1; 149(1):120-6.

Francisco J A, Campbell R, Iverson B L, Georgiou G. Production and fluorescence-activated cell sorting of *Escherichia coli* expressing a functional antibody fragment on the external surface. roc Natl Acad Sci USA. 1993 Nov. 15; 90(22):10444-8.

Greenberg, A S., Avila, D., Hughes, M., Hughes, A., McKinney, E. C. & Flajnik, M. F. A new antigen receptor gene family that undergoes rearrangement and extensive somatic diversification in sharks. *Nature* (London) 374, 168-173, (1995).

Griffiths A D, Williams S C, Hartley O, Tomlinson I M, Waterhouse P, Crosby W L, Kontermann R E, Jones P T, Low N M, Allison T J, et al. (1994). Isolation of high affinity human antibodies directly from large synthetic repertoires. EMBO J., July 15; 13(14):3245-60.

Georgiou, G. et al.; Display of heterologous proteins on the surface of microorganisms: from the screening of combinatorial libraries to live recombinant vaccines. Nat. Biotech., 1997, 15, 29-34.

Gold L, mRNA display: diversity matters during in vitro selection. Proc Natl Acad Sci USA. 2001 Apr. 24; 98(9): 4825-6.

Hamers-Casterman C, Atarhouch T, Muyldermans S, Robinson G, Hamers C, Songa E B, Bendahman N, Hamers R.

Naturally occurring antibodies devoid of light chains. Nature. 1993 Jun. 3; 363(6428):446-8.

Hanes, J., Plückthun, A.; Proc. Natl. Acad. Sci. U.S.A., 1997, 94, 4937-42. Lipovsek, D., Plückthun, A.; J. 1 mm. Methods, 2004, 290, pp 51-67.

Jensen, K. B., Larsen, M., Pedersen, J. S., Christensen, P. A., Alvarez-Vallina, L., Goletz, S., Clark, B. F. and Kristensen, P., 2002. Functional improvement of antibody fragments using a novel phage coat protein III fusion system. Biochem Biophys Res Commun. 298, 566-573.

Kristensen, P. and Winter, G., 1998. Proteolytic selection for protein folding using filamentous bacteriophages. Fold Des. 3, 321-328.

Khosrotehrani and Bianchi, 2005. Multi-lineage potential of fetal cells in maternal tissue: a legacy in reverse. J Cell Sci, 118 (Pt8): 1559-63.

Lu, H., Jin, D. and Kapila, Y. L., 2004. Application of laser capture microdissection to phage display peptide library screening. Oral Surg Oral Med Oral Pathol Oral Radial Endod. 98, 692-697.

McCafferty J, Griffiths A D, Winter G, Chiswell D J. (1990). Phage antibodies: filamentous phage displaying antibody variable domains. Nature. December 6; 348(6301):552-4.

Odegrip R, David Coomber, Bill Eldridge, Rosemarie Hederer, Philip A. Kuhlman, Christopher Ullman, Kevin FitzGerald*, and Duncan McGregor: CIS display: In vitro selection of peptides from libraries of protein—DNA complexes Proc Natl Acad Sci USA. 2004 Mar. 2; 101(9):2806-10

Pack P, Pluckthun A. Miniantibodies: use of amphipathic helices to produce functional, flexibly linked dimeric FV fragments with high avidity in *Escherichia coli*. Biochemistry. 1992 Feb. 18; 31(6):1579-84.

Smith, G P (1985). Filamentous fusion phage: novel expression vectors that display cloned antigens on the viron surface. Science, 228, 1315-1317.

Winter G, Griffiths A D, Hawkins R E, Hoogenboom H R (1994). Making antibodies by phage display technology. Annu Rev Immunol.; 12:433-55.

The invention claimed is:

1. A method of isolating binding members recognizing an antigen of a target cell of limited availability in a heterogeneous mixture of target cells and non-target cells comprising the steps:
   a. identifying the target cells,
   b. contacting said target cells with a binding member generating system that allows linkage between the genotype and the phenotype of the binding member and is selected from the group consisting of: ribosome display, DNA display, yeast display, bacterial display, retroviral display and phage display,
   c. washing said target cells to avoid drying,
   d. protecting binding members associated with said target cells with a shield, wherein the size of said shield is 60-200 μm in width and placed close to the target cells,
   e. minimizing the number of binding members isolated recognizing non-target cells by subjecting the non-target cells to UV light capable of introducing cross-links in the genetic material of the binding members, whereby the genetic information is rendered non-replicable, said shield from step d protecting binding members recognizing a target cell against said UV light, and
   f. isolating binding member(s) recognizing the antigen of the target cell.

2. The method according to claim 1, wherein the ratio of target cells to non-target cells is less than 1/1000.

3. The method according to claim 1, wherein the target cells are limited to one cell.

4. The method according to claim 3, wherein the target cell is a cell in suspension.

5. The method according to claim 3, wherein the target cell is a cell is present on a slide.

6. The method according to claim 3, wherein the target cell is a foetal cell.

7. The method according to claim 6, wherein said shield is a puck or a shadow-stick.

8. The method according to claim 7, wherein a cylinder is used for minimizing reflection of UV light.

9. The method according to claim 1, wherein the target cells are cells in suspension.

10. The method according to claim 1, wherein the target cells are cells present on a slide.

11. The method according to claim 1, wherein the target cells are foetal cells.

12. The method according to claim 11, wherein said shield is a puck or a shadow-stick.

13. The method according to claim 12, wherein a cylinder is used for minimizing reflection of UV light.

14. The method according to claim 1, wherein the binding member is selected from the group of antibodies, antibody fragments and non-immune binding members.

15. The method according to claim 14, wherein the binding member is an antibody.

16. The method according to claim 14, wherein the binding member is an antibody fragment.

17. The method according to claim 14, wherein the binding member is a non-immune binding member.

18. The method of claim 1, wherein said target cells are present in a tissue sample.

19. The method of claim 1, wherein said antigen of a target cell is present in extracellular matrix of the target cell.

* * * * *